United States Patent
Cobb et al.

(10) Patent No.: US 8,251,899 B2
(45) Date of Patent: Aug. 28, 2012

(54) SURGICAL RELEASE APPARATUSES, SYSTEMS AND METHODS

(75) Inventors: Tyson Cobb, Davenport, IA (US); Vince Van Donck, San Diego, CA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 783 days.

(21) Appl. No.: 12/343,651

(22) Filed: Dec. 24, 2008

(65) Prior Publication Data

US 2009/0221876 A1 Sep. 3, 2009

Related U.S. Application Data

(60) Provisional application No. 61/010,358, filed on Jan. 8, 2008.

(51) Int. Cl.
*A61B 1/32* (2006.01)
(52) U.S. Cl. ........................................ 600/201
(58) Field of Classification Search ............... 606/190, 606/167, 170, 179; 600/184, 196, 197, 200–219
See application file for complete search history.

(56) References Cited

U.S. PATENT DOCUMENTS

| | | | | |
|---|---|---|---|---|
| 3,320,948 A | * | 5/1967 | Martin | 600/221 |
| 4,493,321 A | * | 1/1985 | Leather | 606/159 |
| 5,253,659 A | * | 10/1993 | McNamara et al. | 128/898 |
| 5,323,765 A | * | 6/1994 | Brown | 600/104 |
| 5,795,308 A | * | 8/1998 | Russin | 600/567 |
| 5,888,196 A | * | 3/1999 | Bonutti | 600/204 |
| 5,954,671 A | * | 9/1999 | O'Neill | 600/567 |

* cited by examiner

*Primary Examiner* — Eduardo C Robert
*Assistant Examiner* — Summer Kostelnik
(74) *Attorney, Agent, or Firm* — Jenkins, Wilson, Taylor & Hunt, P.A.

(57) ABSTRACT

Surgical release apparatuses, systems and methods are provided. The apparatuses, systems and methods can include one or more cannulas having a base and an insertion body extending from the base with a chamber passing through the base and the insertion body. The cannula can have a movable retractor attached thereto. The retractor configured to facilitate creation of space between the insertion body of the cannula and the retractor. An obturator can be used and can provide a support body configured for insertion into the chamber of the cannula to facilitate the guidance of the cannula. A blade can be provided with a handle, a blade body, and a cutting edge. The blade configured for engaging and being guided by the cannula for the cutting edge to make an incision. One or more spatulas can also be provided. The spatulas can be configured to provide guidance to the blade.

42 Claims, 24 Drawing Sheets

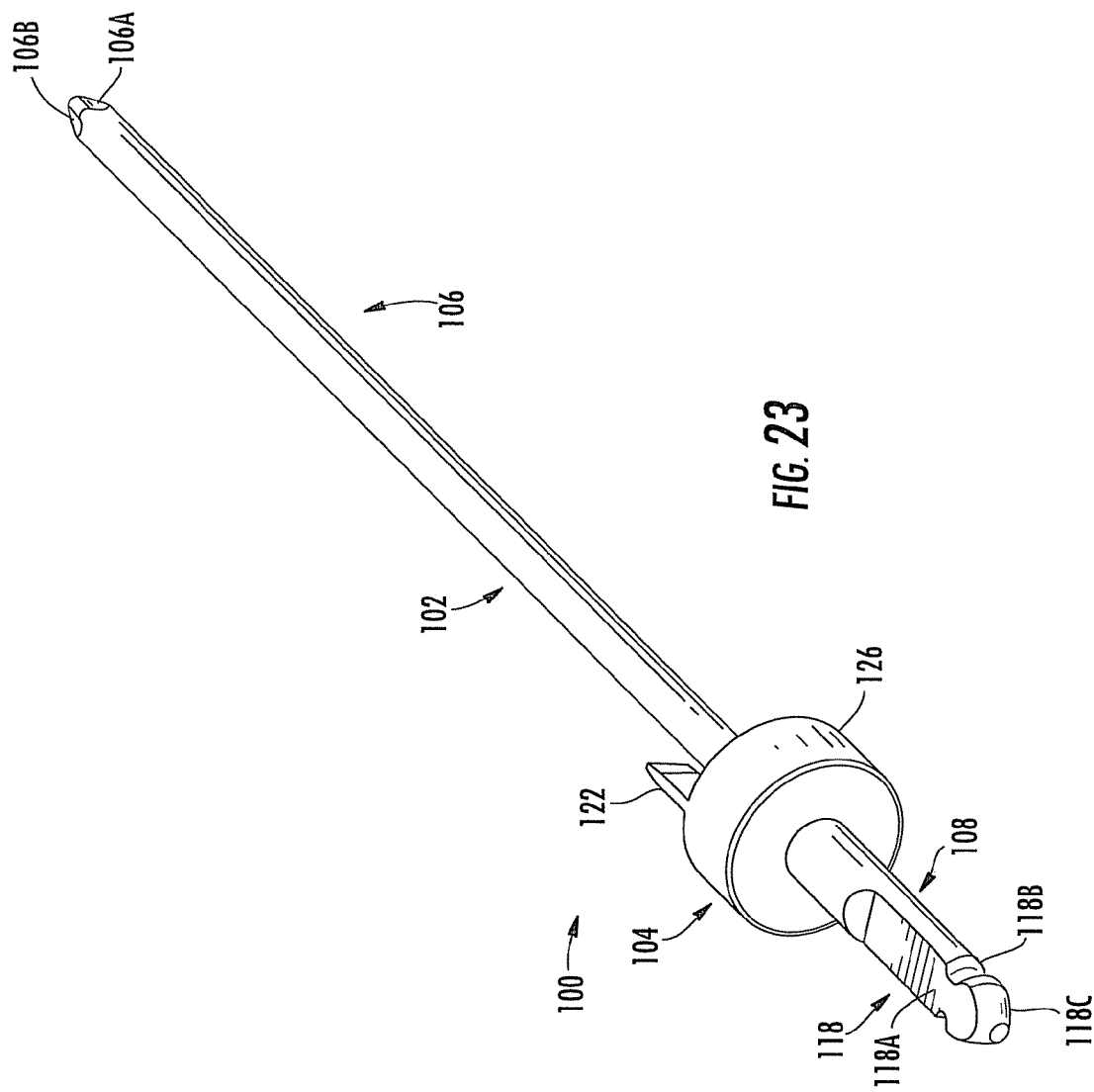

SURGICAL RELEASE APPARATUSES, SYSTEMS AND METHODS

RELATED APPLICATIONS

The presently disclosed subject matter claims the benefit of U.S. Provisional Patent Application Ser. No. 61/010,358, filed Jan. 8, 2008, the disclosure of which is incorporated herein by reference in its entirety.

TECHNICAL FIELD

The subject matter disclosed herein relates generally to apparatuses, systems and methods for endoscopic surgery. More particularly, the subject matter disclosed herein relates to endoscopic apparatuses, systems and methods that can be used, for example, as a treatment for cubital tunnel syndrome to incise the fascia surrounding the ulnar nerve to release pressure from the ulnar nerve.

BACKGROUND

Cubital tunnel syndrome is a condition that affects the ulnar nerve where it crosses the inside edge of the elbow. The symptoms are very similar to the pain resulting from a person hitting his or her funny bone, which is actually the ulnar nerve being hit on the inside of the elbow. There, the ulnar nerve runs through a passage known as the cubital tunnel. When this area becomes irritated such as from injury or pressure, it can lead to cubital tunnel syndrome.

The ulnar nerve actually starts at the side of the neck, where the individual nerve roots leave the spine. The nerve roots exit through small openings between the vertebrae, known as foramen. The nerve roots join together to form three main nerves that travel down the arm to the hand. One of these nerves is the ulnar nerve. The ulnar nerve passes through the cubital tunnel just behind the inside edge of the elbow. The tunnel is formed by muscle, ligament, and bone. The ulnar nerve passes through the cubital tunnel and winds its way down the forearm and into the hand. It supplies feeling to the little finger and half the ring finger and controls the small muscles of the hand.

Because of the importance of hand function in most activities of daily living, the ulnar nerve, which provides the predominant motor innervation to the hand, is perhaps the single most important somatic peripheral nerve in the body. Neuropathy of the ulnar nerve can result in significant disability due to loss of hand function from pain, numbness, and weakness. The most common causes of ulnar nerve neuropathy are entrapment, impingement, stretching, and friction at or around the vicinity of the elbow. Because of the multiplicity of pathological processes that can lead to ulnar neuropathy at the elbow, reviewing its causes and treatment as reported in the medical literature can be confusing and misleading. An example of the diversity of perspectives is the variety of names given throughout the last several decades to describe the phenomenon of ulnar neuropathy at the elbow. This disease process has been referred to as tardy ulnar palsy, traumatic ulnar neuritis, compression neuritis of the ulnar nerve, Feindel-Osborne syndrome, and cubital tunnel syndrome. Tardy ulnar palsy refers only to patients who develop a slow, chronic deterioration of ulnar nerve function months to years after trauma to the elbow. The term cubital tunnel syndrome oversimplifies the ulnar neuropathy at the elbow, which can be due to a number of factors other than compression within the cubital tunnel, such as for example recurrent subluxation of the ulnar nerve out of its groove, or entrapment proximal or distal to the cubital tunnel. The term cubital tunnel syndrome in its broadest sense is a focal neuropathy involving the ulnar nerve in the vicinity of the cubital tunnel.

If modification of habit and/or use of special splints do not relieve the pain caused by the neuropathy, then surgery can be needed to release the nerve. Traditionally, nerve releases have been performed utilizing a long incision on the medial side of the elbow leaving a long scar, usually with some damage to the cutaneous nerves around the elbow and associated morbidity. On the average, a three to four day stay in the hospital was expected. Recently, endoscopic techniques using smaller incisions and requiring less healing time have been developed with varying degrees of success.

SUMMARY

In accordance with this disclosure, surgical release apparatuses, systems and methods are provided. In particular, endoscopic surgical release apparatuses, systems and methods are provided that can be used to incise material including tissue surrounding a nerve to release the pressure caused by inflammation, traumatic injury, or other related sources. As one example, and without limitation, the apparatuses, systems and methods disclosed herein can have particular application for releasing the ulnar nerve in treating cubital tunnel syndrome. It is, therefore, an object of the present disclosure to provide apparatuses, systems and methods that can include a blade, one or more cannulas, one or more obturators, an obturator handle, and one or more spatulas to permit incision of material including tissue surrounding a nerve.

An object of the presently disclosed subject matter has been stated hereinabove and can be achieved in whole or in part by the presently disclosed subject matter. Other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIG. 23 illustrates another perspective view of the embodiment of an obturator according to FIG. 22;

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Figure 1:
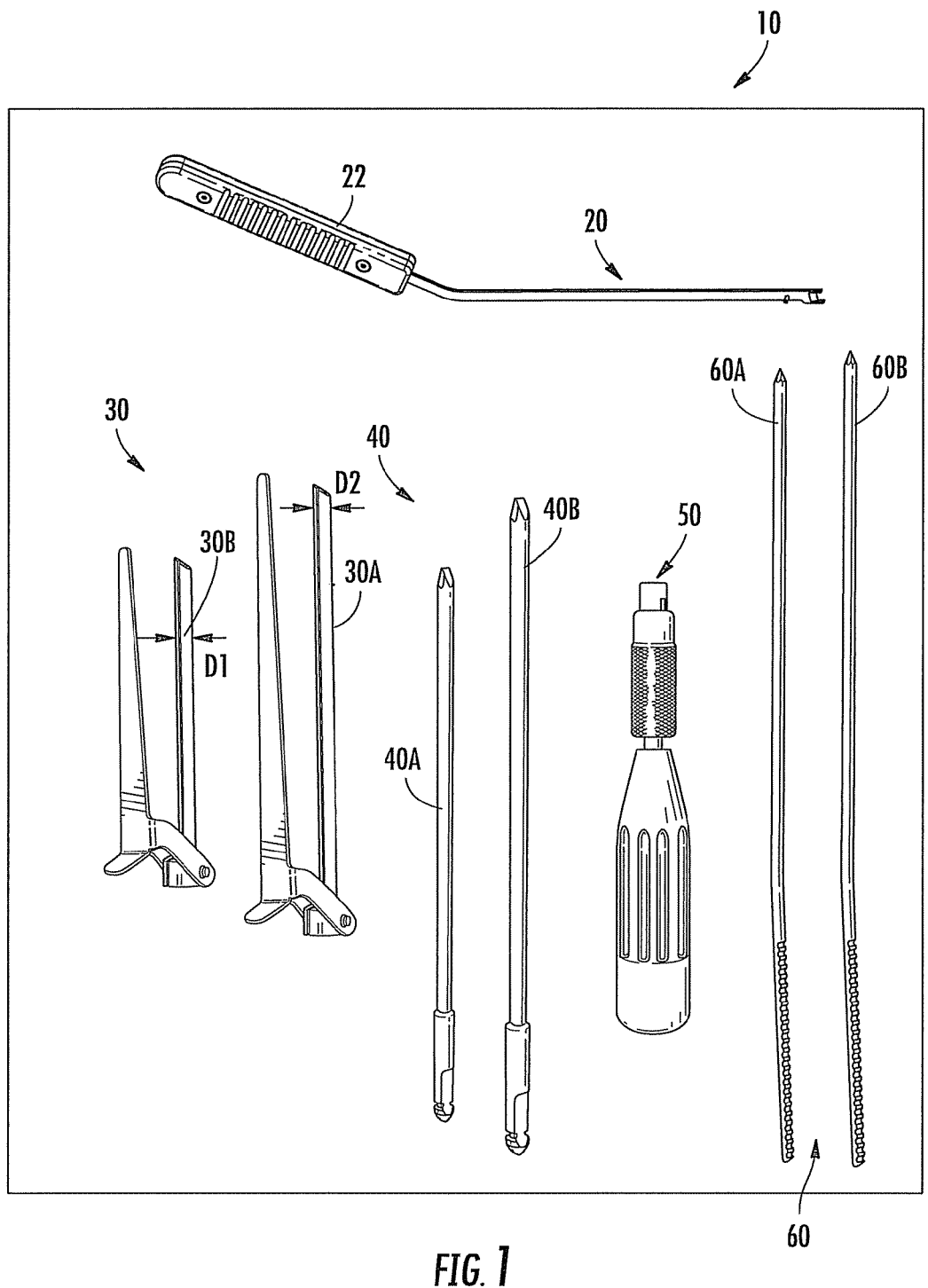
FIG. 1 illustrates a perspective view of embodiments of possible components that can be included in a kit system for use in a release surgery according to the present subject matter.
Figure 2:
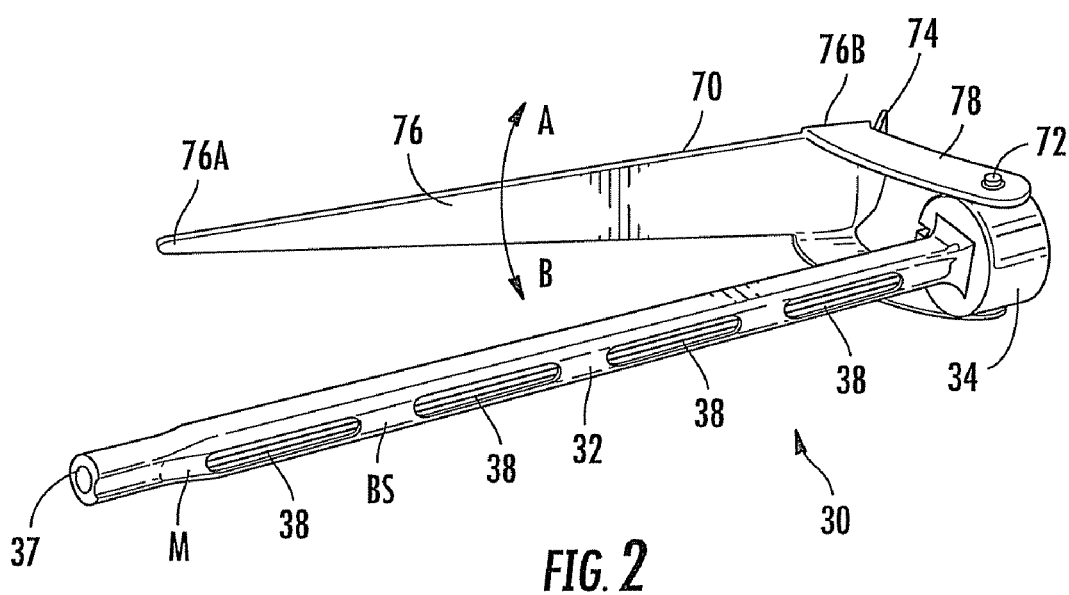
FIG. 2 illustrates a perspective view of an embodiment of a cannula that can be included in accordance with the subject matter herein.
Figure 3:
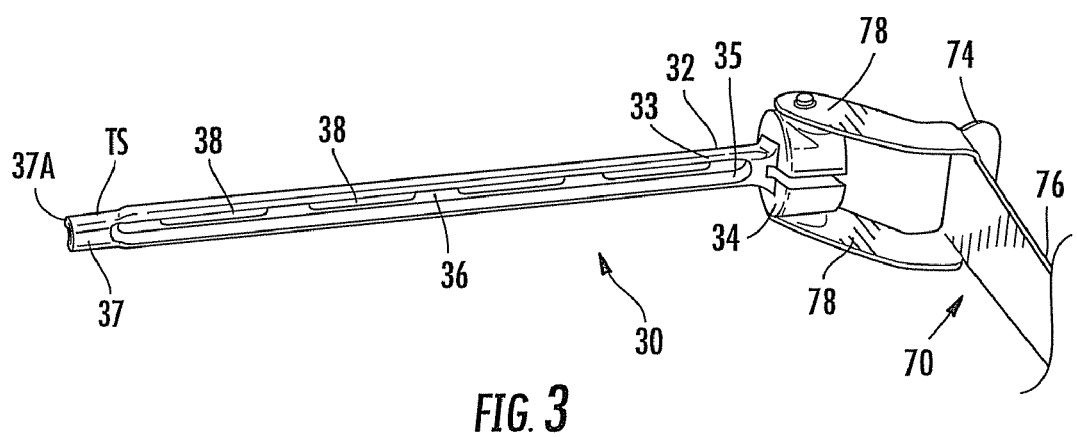
FIG. 3 illustrates another perspective view of an embodiment of a cannula that can be included in accordance with the subject matter herein.
Figure 4:
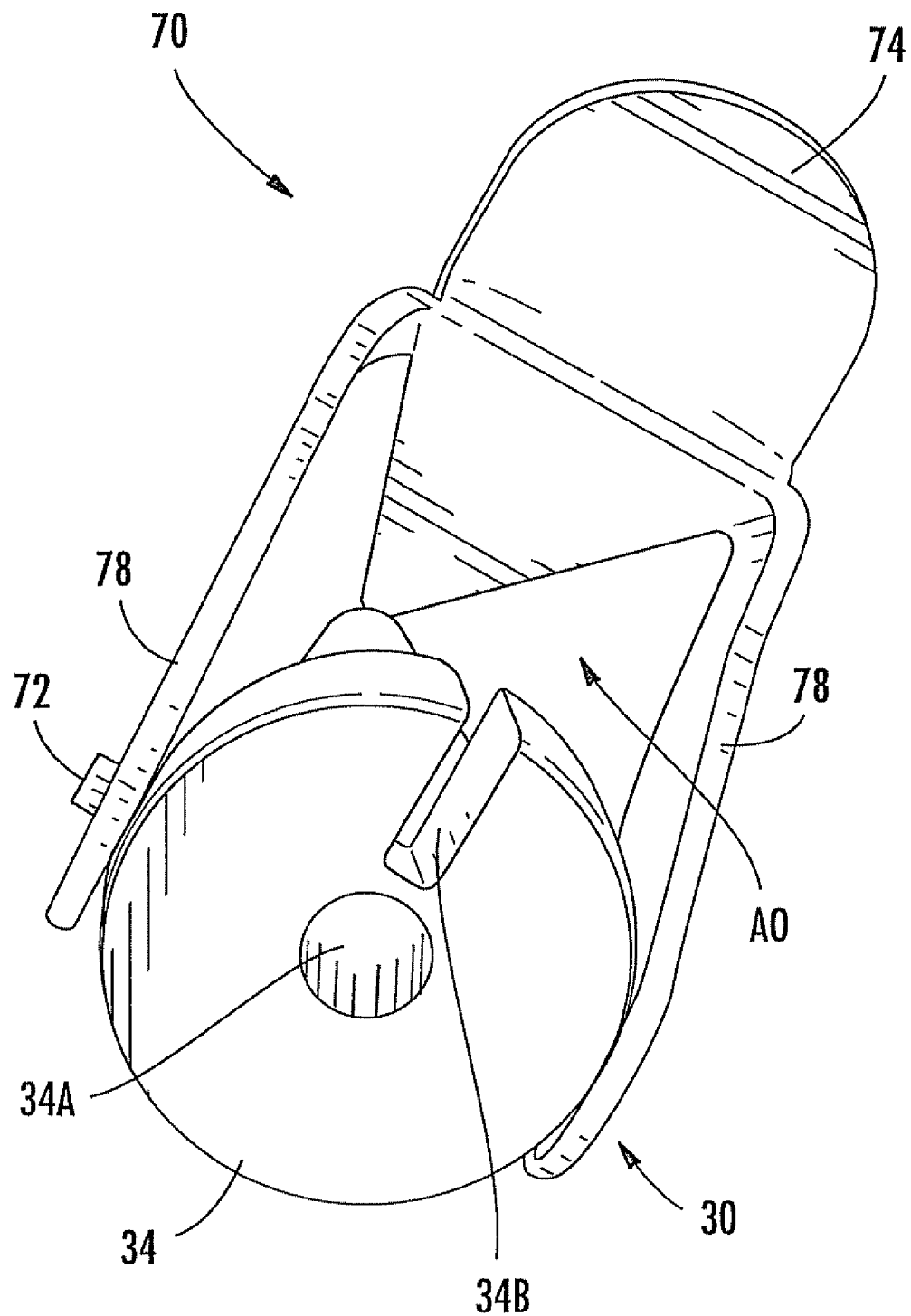
FIG. 4 illustrates an end view of the cannula illustrated according to FIG. 2.
Figure 5:
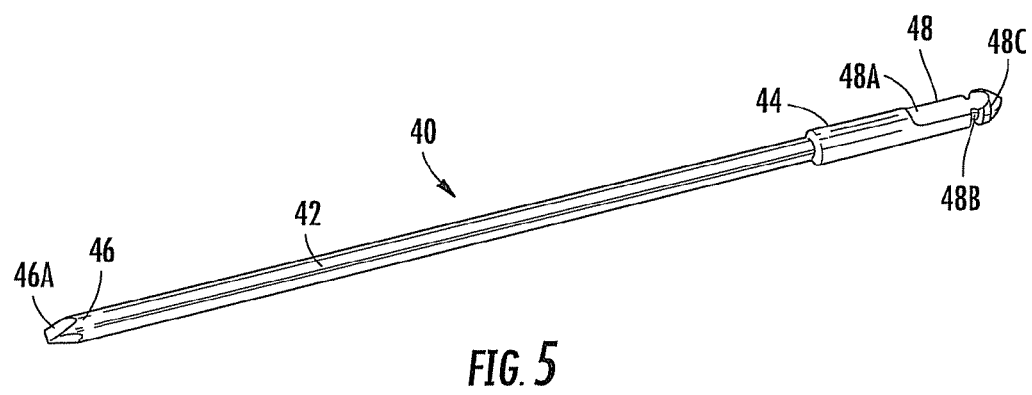
FIG. 5 illustrates a perspective view of an embodiment of an obturator that can be included in accordance with the subject matter herein.
Figure 6:
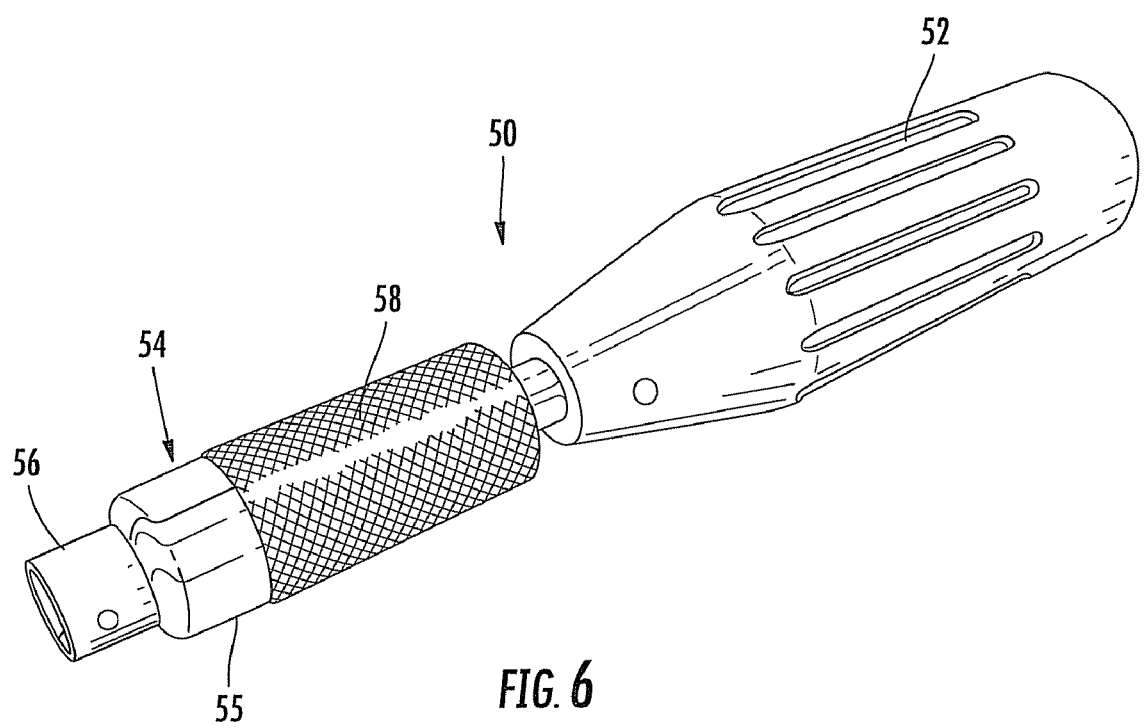
FIG. 6 illustrates a perspective view of an embodiment of an obturator handle that can be included in accordance with the subject matter herein.
Figure 7:
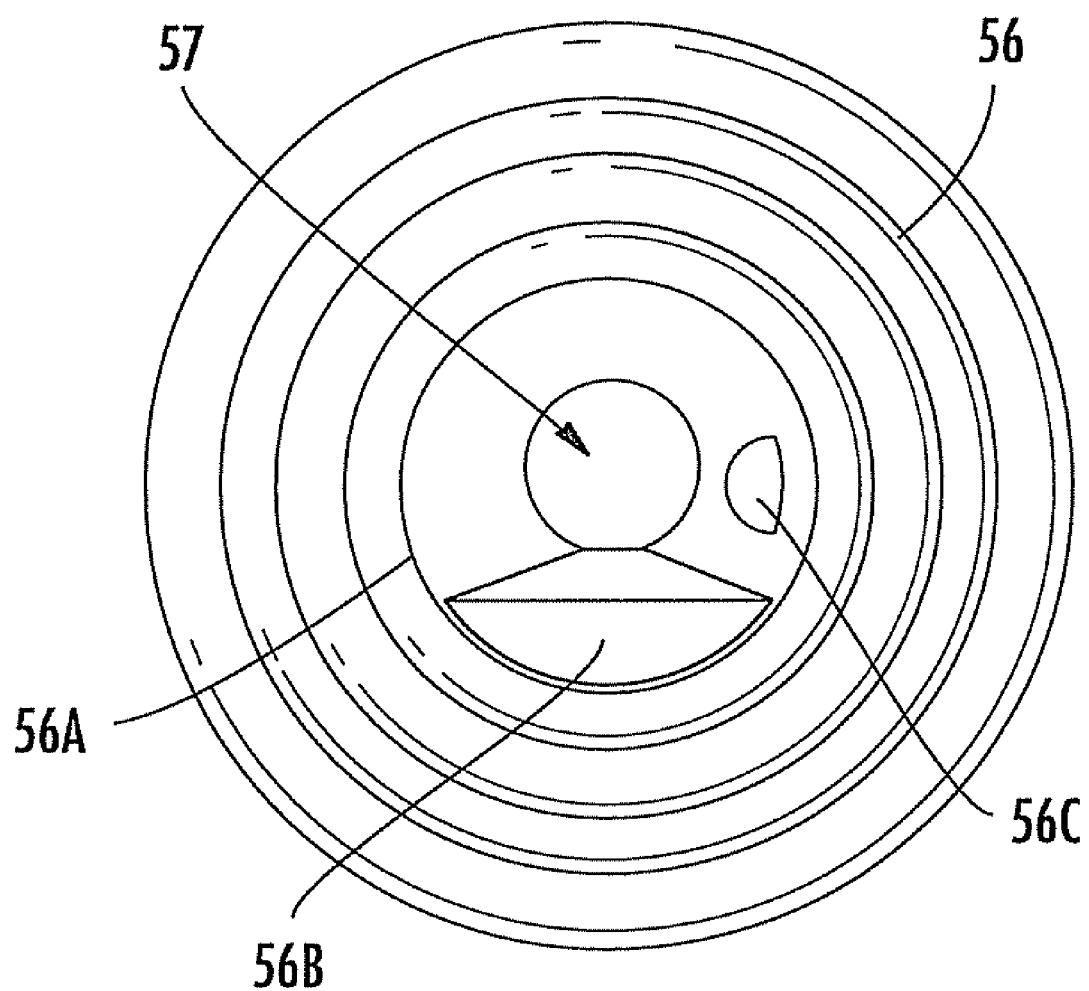
FIG. 7 illustrates an end view of the obturator handle illustrated according to FIG. 6.
Figure 8:
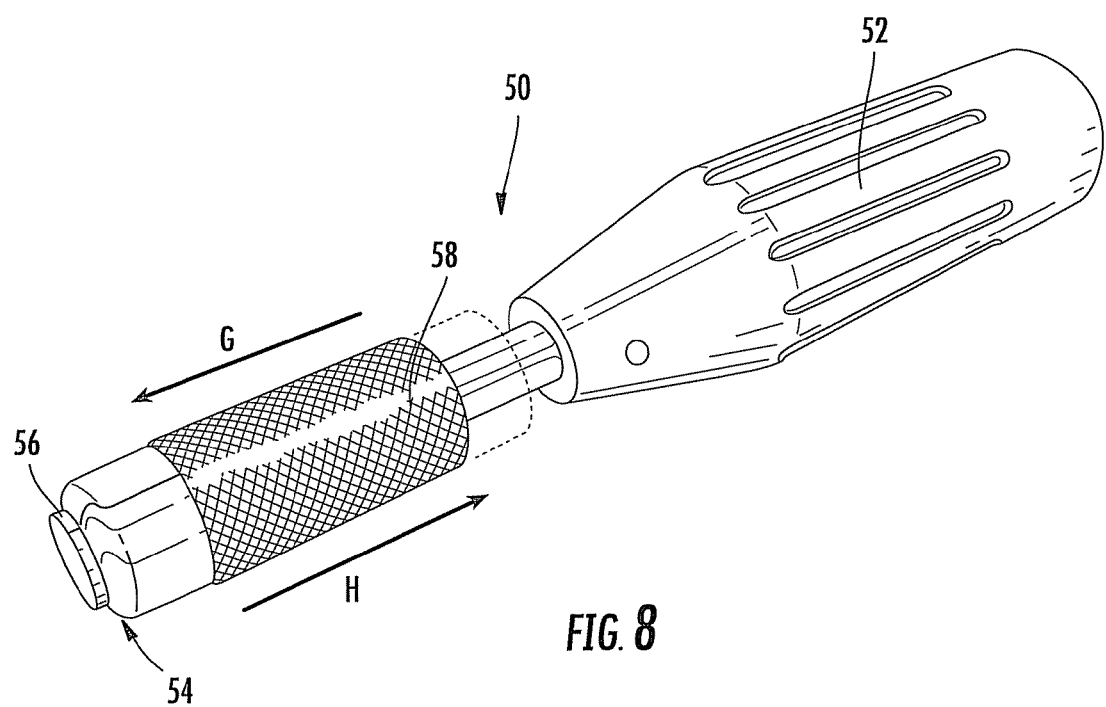
FIG. 8 illustrates a detail view of the obturator handle illustrated according to FIG. 6 showing the grip release motion used to secure and release the obturator within the obturator handle.

FIG. 1 illustrates tools that can be included for example in a kit for release surgery. While the kit and the release systems and apparatuses can be used in a variety of release surgeries, the release systems and apparatuses will be described in conjunction with a cubital tunnel release surgery as an example of how these release systems and apparatuses can be used. Therefore, such release systems and apparatuses should not be limited to use in just cubital tunnel release surgery.

Release system generally designated 10 can be used as described herein to incise the fascia surrounding the ulnar nerve within the cubital tunnel to release the pressure caused by inflammation, traumatic injury or other related sources. Release system 10 can be used with an endoscope to permit a less invasive surgery to occur by allowing a smaller incision around the elbow and less disruption to the cutaneous nerves around the elbow. Such less invasive surgery results in less downtime to the patient and a quicker healing time.

Release system 10 can include a blade 20 with a handle 22, one or more cannula 30 which can have an attached retractor, one or more obturator 40, an obturator handle 50, and optionally one or more spatula 60. For example, two sizes of the cannula 30, obturator 40, and spatula 60 can be included in release system 10. A large cannula 30A and a small cannula 30B can be provided. A large obturator 40A and a small obturator 40B can be provided. Similarly, a large spatula 60A and a small spatula 60B can be provided. The different sizes of reusable cannulas, obturators, and spatulas permit a single kit release system 10 to be used on a wide range of patients. Small cannula 30B, small obturator 40B, and small spatula 60B can be used on a range of smaller sized patients, while large cannula 30B, large obturator 40B, and large spatula 60B can be used on a range of larger sized patients. The cannulas, obturators, obturator handle, and spatulas can be provided non-sterile and designed for repeated sterilization in a surgical setting. The blade 20 with handle 22 can be provided sterile and can be for single use only.

As described above, the apparatuses or tools of release system 10 can be designed to be used with an endoscope. A surgeon can insert a cannula 30, which can also acts as a retractor, into an incision around the elbow. An obturator 40 can be inserted into the cannula 30 to position the cannula 30 into the cubital tunnel. Obturator 40 can then be removed and the endoscope can be inserted to visualize the ulnar nerve and the fascia that is to be cut that surrounds the ulnar nerve. Blade 20 can be inserted into the cannula 30 and the fascia can be incised as described further herein. In this manner, release system 10 can be used in the endoscopic surgical treatment of cubital tunnel syndrome by releasing the fascia around the ulnar nerve.

Figure 12:
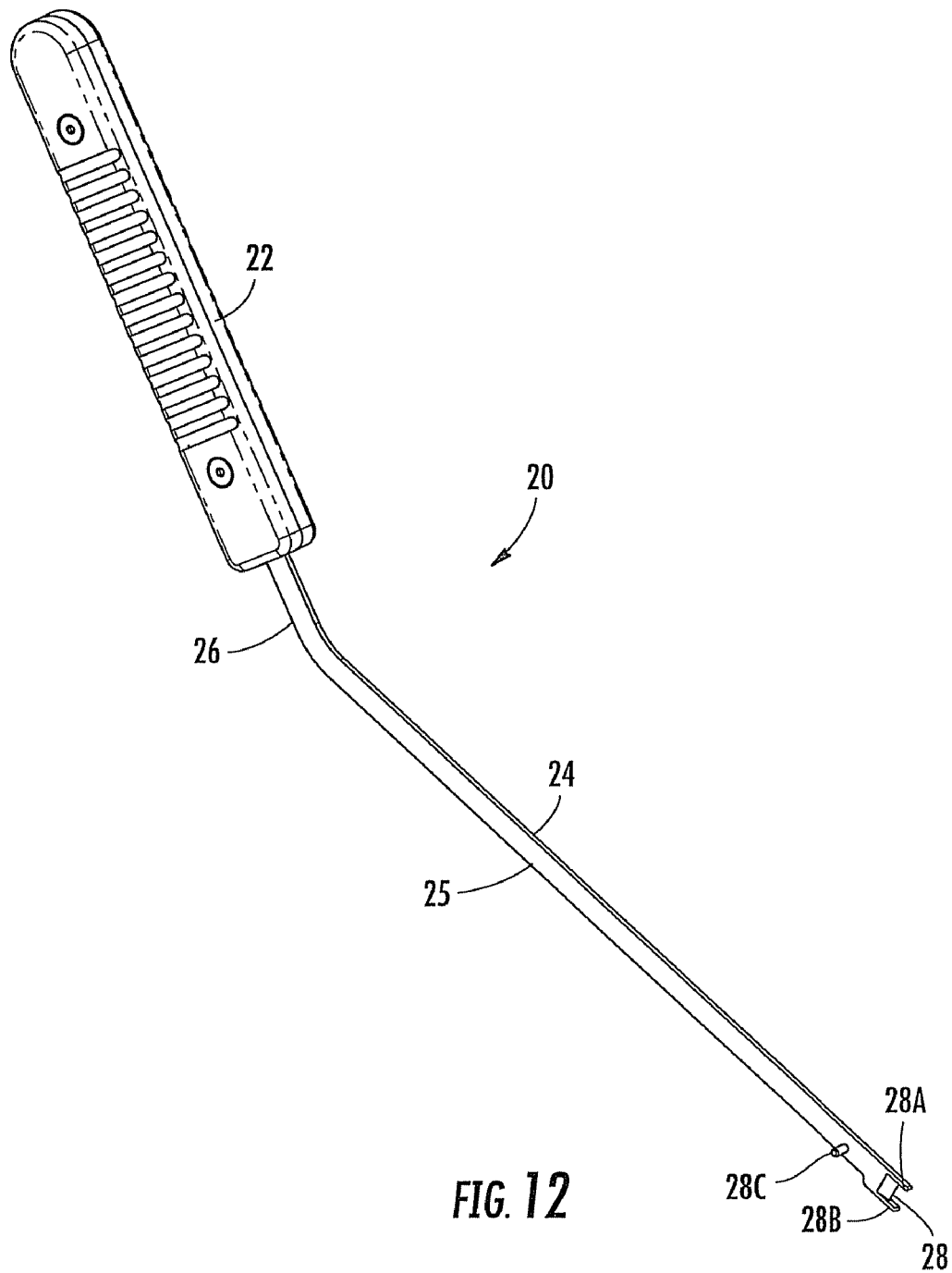
FIG. 12 illustrates a perspective view of an embodiment of blade with a handle that can be included in accordance with the subject matter herein.
Figure 13:
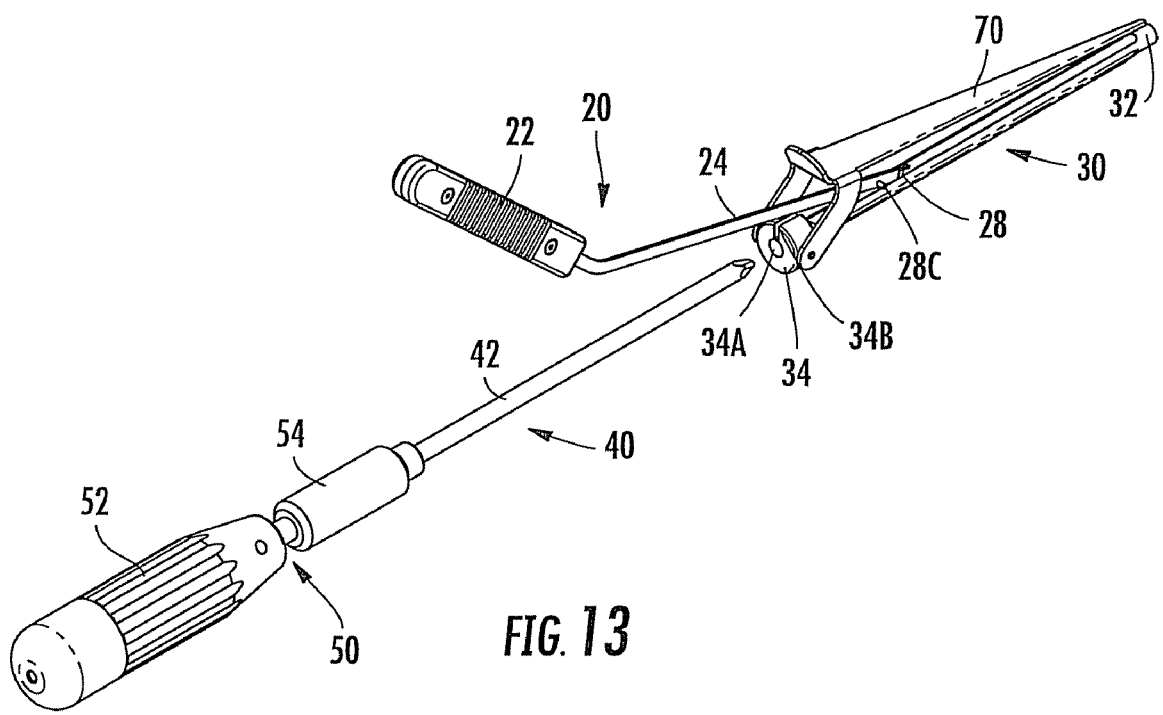
FIG. 13 illustrates a perspective view of an embodiment of a cubital tunnel blade assembly with a cannula according to the present subject matter.

With FIGS. 1-15, some possible components of release system 10 are explained in more detail. Blade 20 with handle 22 can be a single-use product that is individually packaged in a sterilized packaging. As shown in FIGS. 12-14, blade 20 can have a body 24 that can extend outward from handle 22. Body 24 can have a working length 25 and a bend 26 so that blade 20 extends at an angle such as at an angle that increases optimization of the cutting. At the end of working length 25 of body 24, a protected cutting edge 28 can be provided. Blade 20 can be used for endoscopic surgery with a cannula 30 and an obturator 40 as a cutting system. Cutting edge 28 of blade 20 can be used to transect the fascia surrounding the ulnar nerve, resulting in relief of pressure on the nerve. Cannulas 30, obturators 40, and spatulas 60 are designed to aid in precision cutting by cutting edge 28 and reduce risk of damaging the ulnar nerve and surrounding soft tissue.

Prior to use, the integrity of a package containing a blade 20 to be used should be inspected for damage that may compromise sterility of the device. If damaged, sterility may be compromised and blade 20 should not be used. Blade 20 can be designed and provided as a single-use, disposable product and should not be re-sterilized. Once used, blade 20 should be discarded.

Straight working length 25 of body 24 of blade 20 can be about 10.0 cm in length with protected cutting edge 28 having a length of about 3.0 mm. Safety prongs 28A, 28B can extend from blade 20 on either side of cutting edge 28 to protect the cutting edge 28. Safety prongs 28A, 28B can extend about 0.5 mm from the cutting edge 28. The cutting edge 28 of blade 20 can be an ultra sharp cutting edge between safety prongs 28A, 28B. Further, working length 25 can include guides 28C which can protrude from either side of body 24 of blade 20. Guides 28C can help guide blade 20 in cannula 30 by residing against sides 33 of a continuous slot 36 in cannula 30 that can be used to guide blade 20. However, it should be noted that guides are not required and in other embodiments can be omitted entirely.

Handle 22 of blade 20 can be an ergonomic, no-slip handle. Blade 20 can be made from a variety of suitable and different types of materials. For example, blade 20 can be made from a rust-proof stainless steel, for instance, 440A stainless steel. Handle 22 of blade 20 can be made of a plastic material. For example, handle 22 can be made from a thermoplastic material such as a polyester, polypropylene, polyethylene, or the like. In one embodiment, handle 22 can be a low density polyethylene. As described above, unlike the blade 20, cannulas 30, obturators 40, obturator handle 50, and spatulas 60 can be resterilized.

Referring to FIGS. 2-4, 13, and 15, each cannula 30 can include an insertion body 32 and a base 34. Insertion body 32 can define a lead end 37. A chamber 35 can exist and be defined through both insertion body 32 and base 34 between an aperture 34A in the base 34 and an aperture 37A in the lead end 37. The apertures 34A, 37A and chamber 35 can receive an obturator 40 and/or an endoscope 80. Each cannula 30 can be slotted to provide a guide for blade 20 and to provide a view of the ulnar nerve for endoscope 80 to pick up. For example, continuous open slot 36 through a top surface TS of cannula 30 can be used for providing guidance to blade 20 in cutting of the fascia. Continuous slot 36 can extend in insertion body 32 from a position close to base end 35 up to lead end. In such an embodiment, continuous slot 36 does not have to extend through lead end 37. A series of open slots 38 can also be provided on the bottom M of cannula 30 passing through a bottom surface BS for viewing the ulnar nerve if used with endoscope 80. Slots 38 can be spaced apart at a distance that allows a good visualization of the nerve to the surgeon, while not compromising the structural integrity of cannula 30. Bottom surface BS can be any suitable shape. For example, bottom surface BS can be substantially flat, concave, or of another suitable configuration. For instance, bottom surface BS of cannula 30 can be concave for better positioning above a nerve, with a concavity of bottom surface BS that can have a radius to help keep the nerve under cannula 30 and out of harms way while fascia is release with blade 20.

Each cannula 30 can have a tissue retractor, generally designated 70, integral thereto to facilitate use by one person. In such an embodiment, cannula 30 can operate as a retractor that can separate the edges of a surgical incision and hold back underlying tissues to provide a safe working space for the release to be performed with blade 20. Retractor 70 can include a trigger 74, retractor arm 76 and separator supports 78. Retractor 70 can be secured to cannula 30 at pivotal points 72 that permit rotational movement of the retractor arm 76 in directions A and B by movement of trigger 34. In this manner, retractor arm 76 can be moved to different positions relative to insertion body 32 of cannula 30. Retractor arm 76 can have a lead end 76A and a base end 76B. Lead end 76A of the retractor arm 76 can be narrower than base end 76B and can have a width that can be similar to the width of lead end 37 of insertion body 34 of cannula 30 to facilitate insertion into the surgical incision.

Separator supports 78 can extend down from base end 76B to secure retractor 70 to base 34 of the cannula 30 at pivot points 72 to create an access opening AO. Base end 76B of retractor arm 76 can be wider than lead end 76A to add girth to retractor 70 and to increase the size of access opening AO. Base end 78 can be similar in width to base 34 of cannula 30.

Base 34 of cannula 30 can also include a guide slot 34B for guiding blade 20 once it is inserted through access opening AO and resides in continuous slot 36. The width of guide slot 34B can be such that working length 25 of body 24 of blade 20 can fit snugly with guide slot 34B to provide precise guidance to blade 20 while not creating any undue friction between blade 20 and cannula 30.

Figure 15:
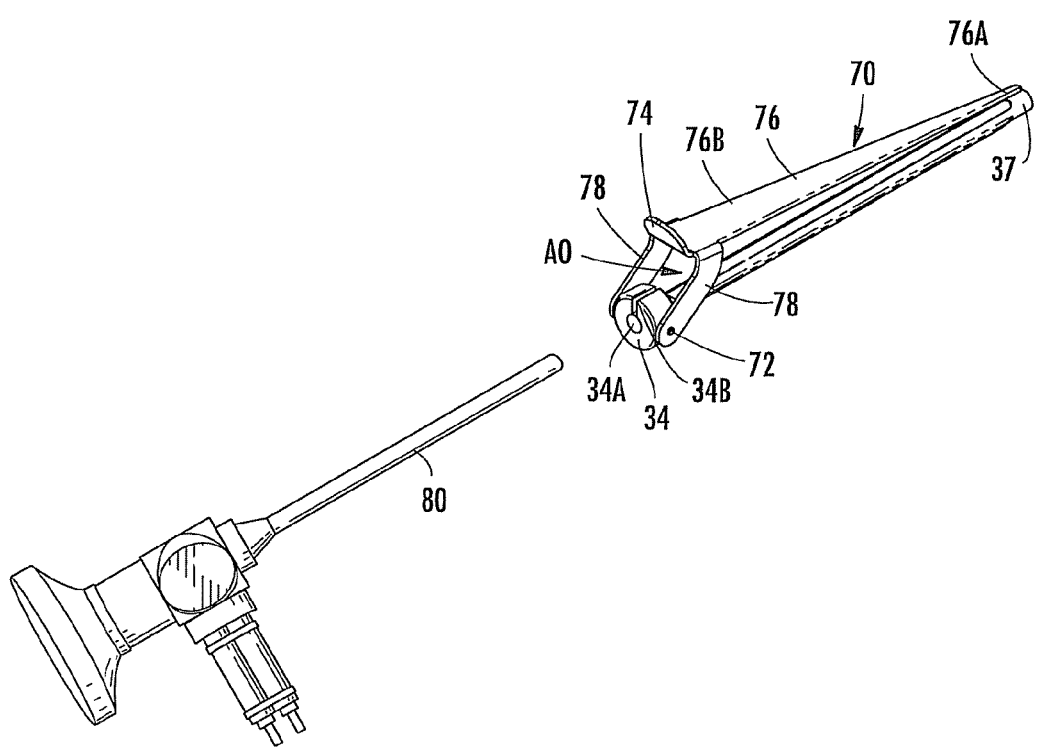
FIG. 15 illustrates a perspective view of an embodiment of a cannula with an endoscope inserted into the cannula according to the present subject matter.
Figure 16:
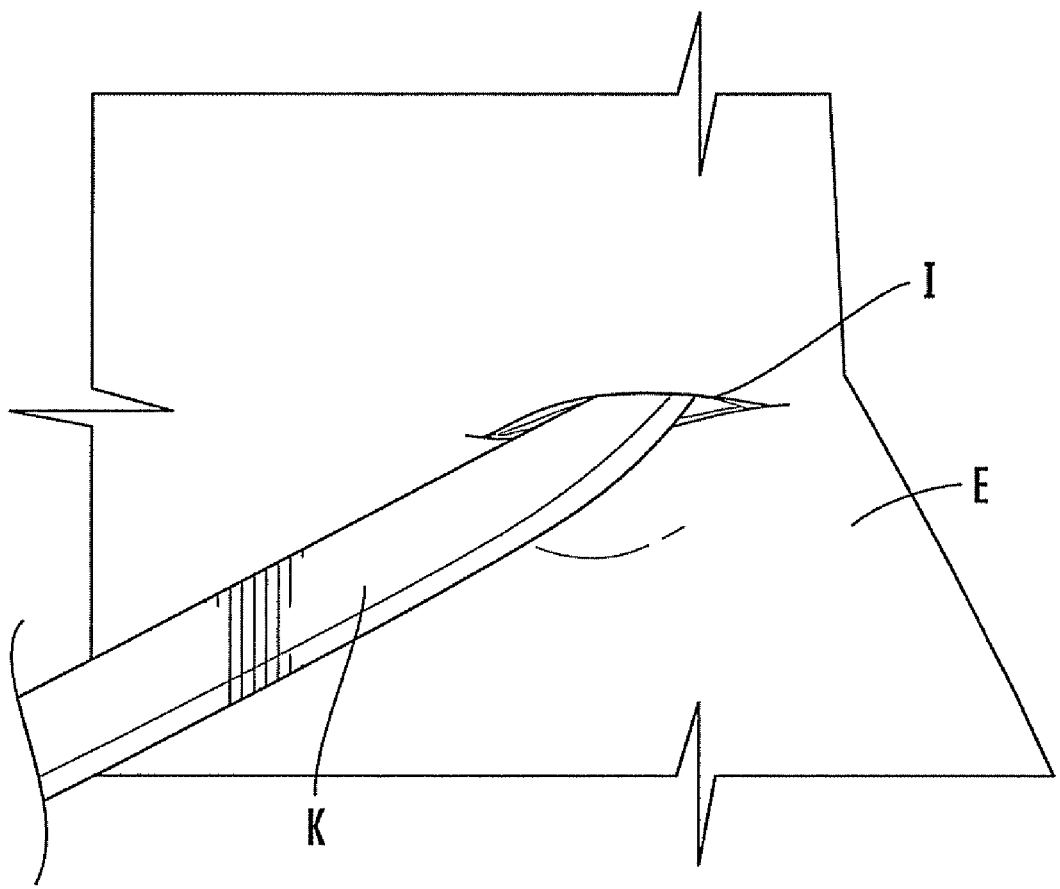
FIGS. 16-20, 21A and 21B illustrate use the tools of a release system in accordance with the subject matter herein to perform a release surgery.
Figure 17:
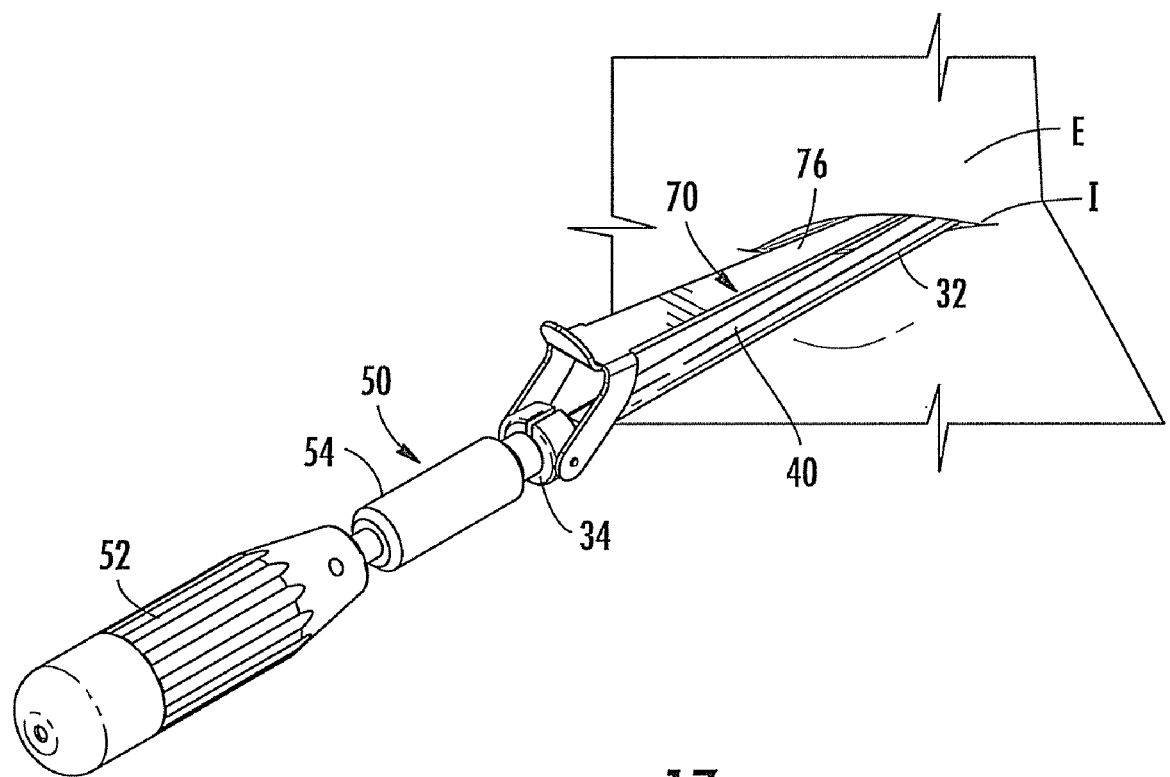
Figure 18:
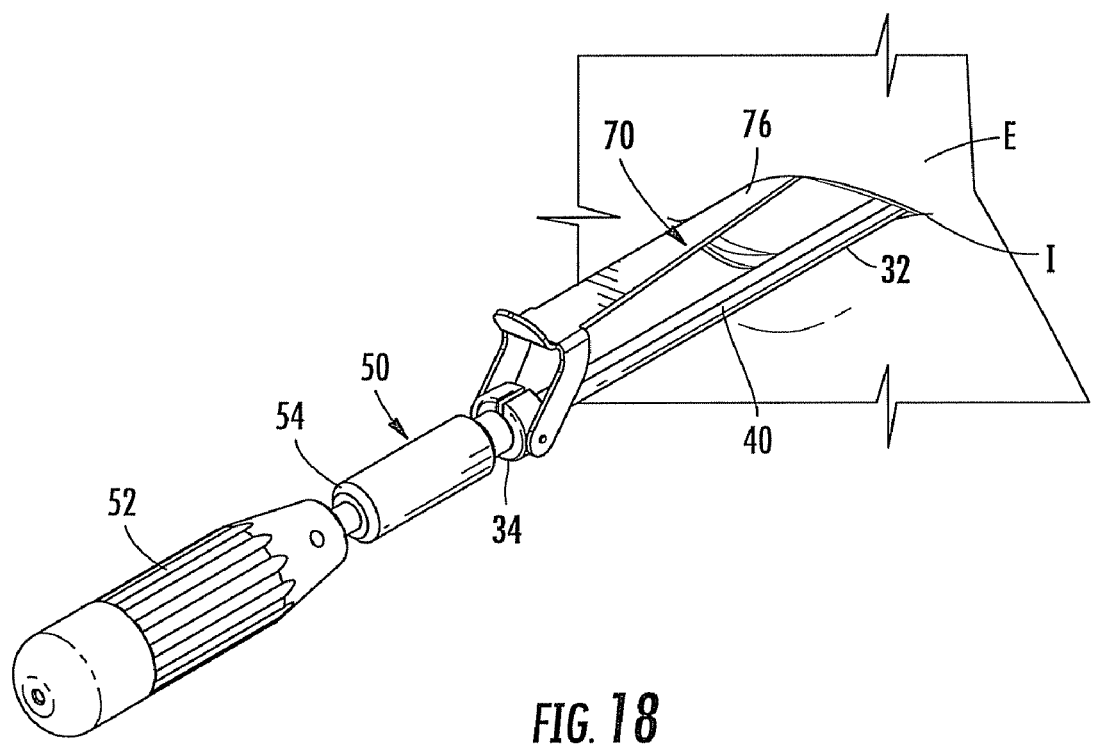
Figure 19:
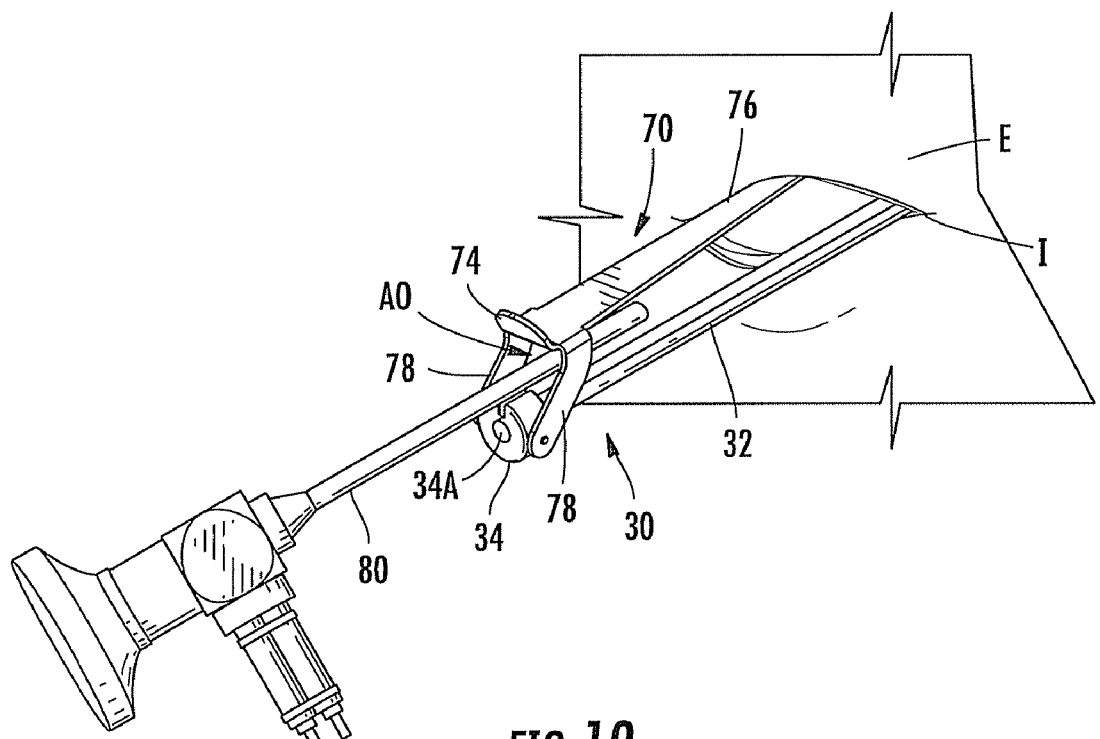
Figure 20:
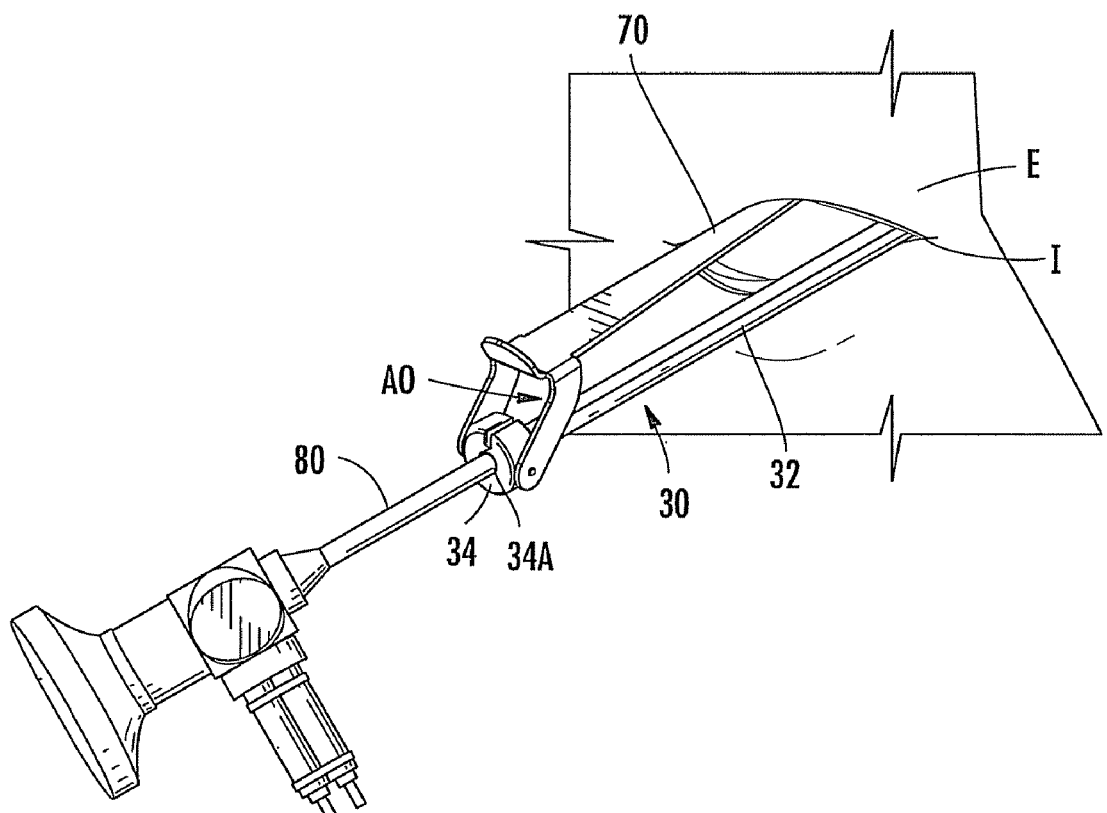

Endoscope 80, as shown in FIG. 15, can be inserted into chamber 35 in some instances during surgery. Additionally or alternatively, endoscope 80 can be inserted in access opening AO to provide a different perspective at different points during surgery.

As stated above and shown in FIG. 1, two cannulas 30A, 30B of different sizes can be provided. Small cannula 30B can have an outer diameter $D_1$ at a lead end 37 that can be provided with an inner diameter that allows for a 2.7 mm endoscope to be inserted therein. For example, outer diameter $D_1$ can be about 4.75 mm or less. The length of the small cannula 30B can be about 8.5 cm. Large cannula 30A can have an outer diameter $D_2$ at a lead end 37 that permits an inner diameter that allows for a 4.0 mm endoscope to be inserted therein. For example, outer diameter $D_2$ can be between about 4.75 mm and about 6.0 mm. The length of the large cannula 30A can be about 11.5 cm.

Cannulas 30 can be made from surgical grade stainless steel. Surgical grade stainless steel has been shown to have a proven clinical history and is traceable to accepted material standards for bio-compatibility, strength, etc. Further, surgical grade stainless steel can be sterilized in a surgical setting.

Referring to FIGS. 5-10, and 13, obturator 40 and obturator handle 50 will be described in more detail. Obturator 40 provides support for cannula 30 during insertion into the body of the patient and provides a lead point 46A for guiding the insertion of the corresponding cannula 30. Each obturator 40 can include a support body 42 and a handle insert 44. Handle insert 44 can be thicker in diameter than support body 42. Support body 42 of obturator 40 can have a head end 46. Head end 46 of obturator 40 can have angled surfaces that end in a relatively blunt lead point 46A to serve as a lead in for the device. For example, head end 46 can have four angled surfaces to help lead in the device. These angled surfaces preferably do not have sharp edges.

Each obturator 40 can be provided with handle insert 44 which can have a coupling configuration 48. The coupling configuration 48 can be accepted by a standard A/O couple within obturator handle 50. For example, coupling configuration 48 can include a keyway 48A. Keyway 48A can extend over the entire width of handle insert 44. A groove 48B can extend around the remaining circumference of handle insert 44. The distal end of handle insert 44 can have tapered sides 48C. Keyway 48A, groove 48B and/or the tapered sides 48C of the coupling configuration 48 can all help to secure obturator 40 to obturator handle 50 through the couple therein.

Obturator handle 50 can include a grip 52 and a locking chamber portion 54. The locking chamber portion 54 can include a standard A/O couple handle used within the surgical art. For example, the locking chamber portion can include slide barrel 55 and a receiving end 56. Slide barrel 55 can be spring loaded and can include a grip surface 58 to facilitate the surgeon's grip to permit slide barrel 55 to be pushed forward in a direction G. The spring therein can bias slide barrel 55 in the direction H toward grip 52.

Receiving end 56 defines an aperture 56A and chamber 57 therein to receive the coupling configuration 48 of handle insert 44 of obturator 40. Receiving chamber 57 can extend through obturator handle 50. Receiving end 56 can have a key 56B that can mate with keyway 48A of handle insert 44. If keyway 48A aligns with key 56B, then tapered sides 48C can pass into aperture 56A without obstruction. Receiving end 56 can also include at least one spring-loaded locking ball 56C that can be depressible into the wall of chamber 57, but is biased out into chamber 57. As tapered sides 48C of handle insert 44 pass locking ball 56C, tapered sides 48C can depress locking ball 56C at such positions along tapered sides 48C of sufficient width to allow tapered sides 48 to pass locking ball 56C. After tapered sides 48C pass locking ball 56C, locking ball 56C can spring into groove 48B to effectively lock obturator 40 into obturator handle 50. To release obturator 40 from obturator handle 50, slide barrel 55 can be configured to engage locking ball 56C so that when slide barrel 55 is pushed forward in direction G, locking ball 56C is withdrawal into chamber 57. In this manner, handle insert 44 and obturator 40 can be released from obturator handle 50.

Figure 9:
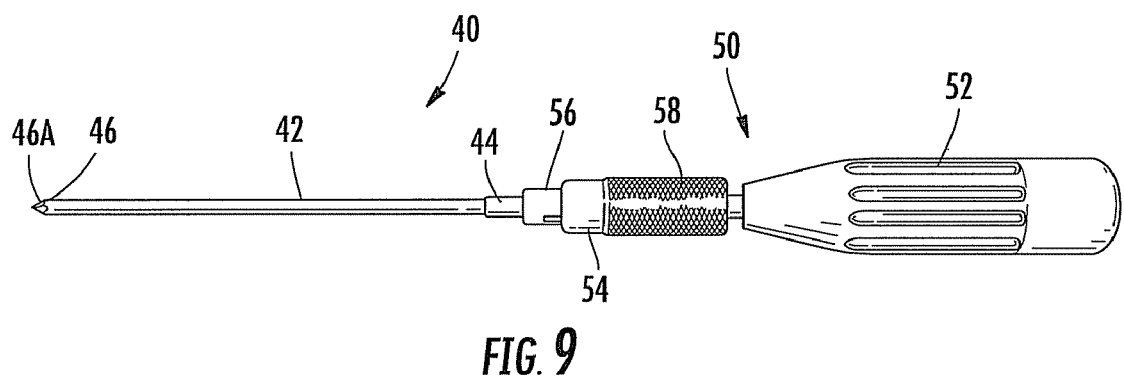
FIG. 9 illustrates a perspective view of the obturator and the obturator handle combined for use according to FIGS. 5 and 6.
Figure 10:
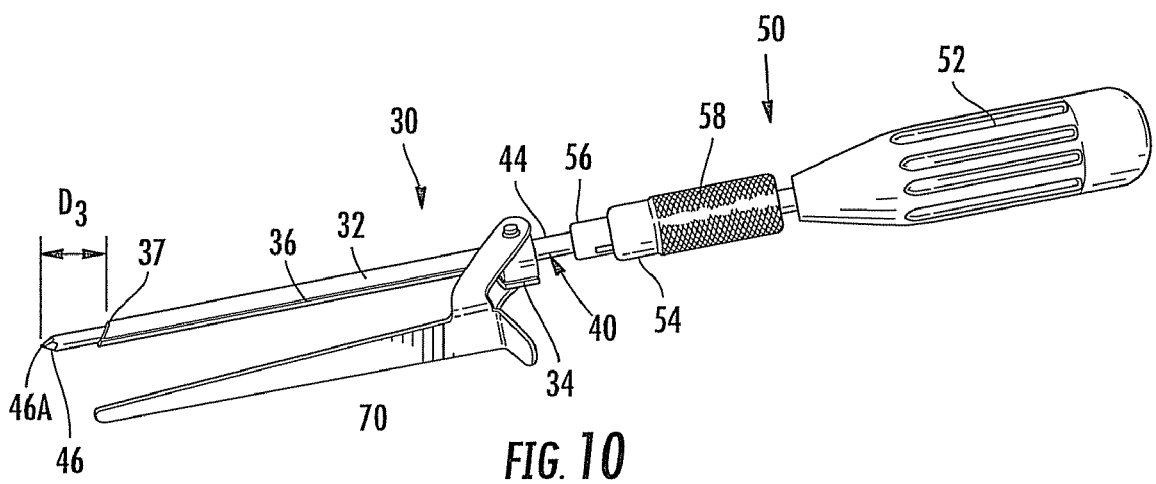
FIG. 10 illustrates a perspective view of the obturator with the obturator handle according to FIG. 9 inserted in the cannula according to FIG. 2.

As seen in FIGS. 9 and 10, support body 42 of obturator 40 can be inserted through the aperture in base 34 and chamber 35 of cannula 30 such that head end 46 extends out through the aperture in lead end 37 of cannula 30. Head end 46 with its angled surfaces and lead point 46A facilitates guiding cannula 30 to the proper location within the elbow between the ulnar nerve and the fascia surrounding it. Further, the rest of support body 42 of obturator 40 buttresses insertion body 32 of cannula 30 during insertion into the elbow of the patient.

The diameter of each obturator 40 can be configured to fit snugly inside the inner diameter of the respective corresponding cannula 30. The effective length of each obturator 40 can be such that it extends past lead end 37 of the respective corresponding cannula 30 by a distance $D_3$ to provide an unobstructed head end 46 and lead point 46A of obturator 40 for guiding the insertion. For example, the effective length of a large obturator can be such that distance $D_3$ from lead point 46A of head end 46 to lead end 37 of the large cannula can be about 7 mm to about 8 mm. The effective length of a small obturator can be such that distance $D_3$ from lead point 46A of head end 46 to lead end 37 of the small cannula can be about 5 mm to about 6 mm. Other effective lengths for an obturator can be used for other, suitable distances.

As with cannulas 30, obturators 40 can be made from surgical grade stainless steel. Surgical grade stainless steel has been shown to have a proven clinical history and is traceable to accepted material standards for bio-compatibility, strength, etc. Further, surgical grade stainless steel can be sterilized in a surgical setting.

Figure 11:
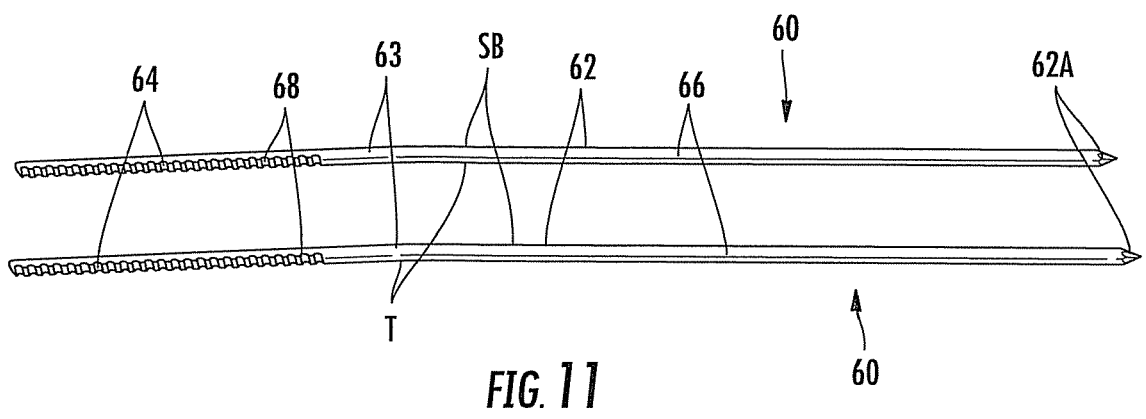
FIG. 11 illustrates a perspective view of an embodiment of spatula that can be included in accordance with the subject matter herein.
Figure 14A:
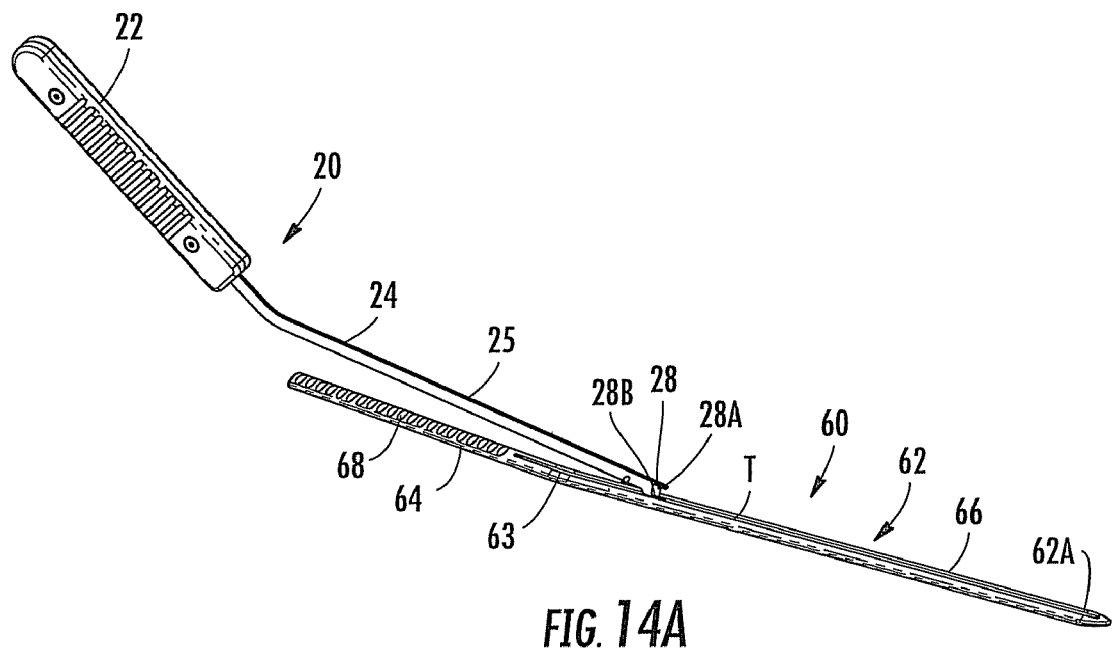
FIG. 14A illustrates a perspective view of an embodiment of a blade with an embodiment of a spatula according to the present subject matter.
Figure 14B:
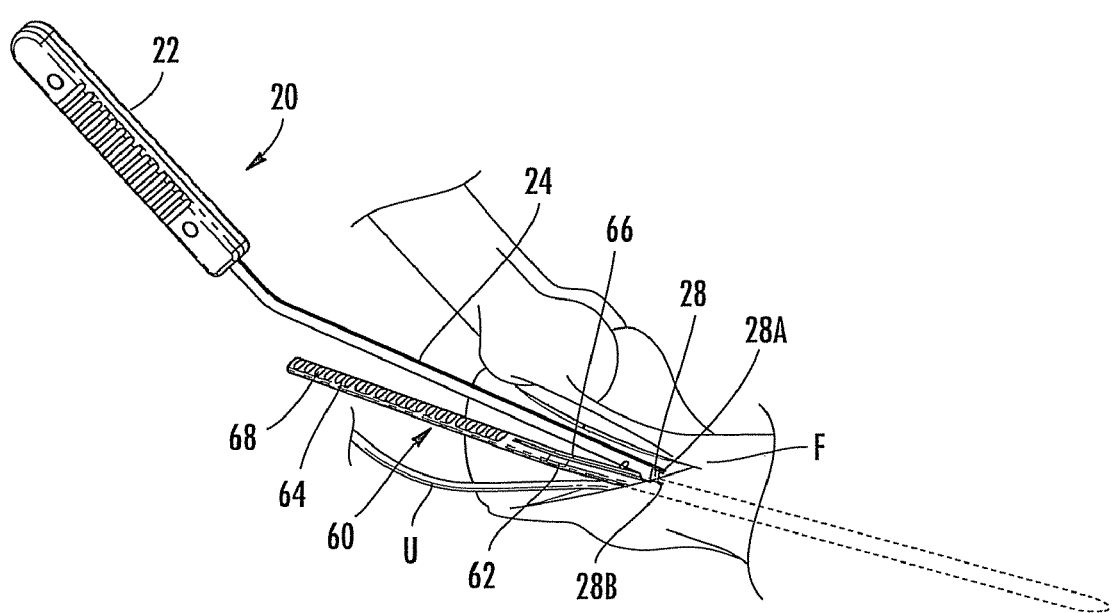
FIG. 14B illustrates a perspective view of an embodiment of a blade with an embodiment of a spatula during use according to the present subject matter.

Referring to FIGS. 11, 14A and 14B, each spatula 60 can include a guide portion 62 and a grip portion 64. Grip portion 64 can include a textured surface 68 on a top T to provide a place for a surgeon to get a stable and tight grip on a spatula 60. Spatula 60 can have a curved bottom SB. Guide portion 62 can include a blade groove 66 that can extend down to head point 62A of spatula 60.

FIG. 14A shows blade 20 engaging spatula 60. FIG. 14B shows blade 20 engaging spatula 60, while spatula 60 is placed between fascia F and ulnar nerve U. Curved bottom SB of spatula 60 can reside overtop ulnar nerve U once spatula 60 is inserted between fascia F and ulnar nerve U. Blade groove 66 in each spatula 60 can be used to guide blade 20 while cutting fascia F. Bottom safety prong 28B of cutting edge 28 can ride along groove 66 to guide blade 20 during cutting.

Spatula 60 can be slightly angled between guide portion 62 and grip portion 64. For example, spatula 60 can be bent at an angle at a point such as point 63 between guide portion 62 and grip portion 64. The lengths of each spatula 60 should be such that they can provide guidance for the blade during cutting of the fascia to provide complete release of ulnar nerve along the cubital tunnel. For example, the length of each spatula 60 can be about 196 mm to about 200 mm. The width of each spatula 60 should be such that it provides the necessary guidance to blade 20 during cutting while minimizing the intrusiveness of each spatula 60 within the surgical area. For example, for the small spatula, the width can be about 5 mm, and for the large spatula, the width can be about 7 mm.

As with the cannulas 30 and obturators 40, spatulas 60 can be made from surgical grade stainless steel. Surgical grade stainless steel has been shown to have a proven clinical history and is traceable to accepted material standards for bio-compatibility, strength, etc. Further, surgical grade stainless steel can be sterilized in a surgical setting.

Generally, the users of such a release system 10 can be orthopedic surgeons, orthopedic hand specialists, reconstructive plastic surgeons, and/or trauma doctors. Release system 10 can come with a package insert. The packaging should be easy to open and used in the sterile surgical environment. System 10 can facilitate operation by one person. System 10 can also facilitate a minimally invasive procedure to minimize complications. System 10 is designed to minimize trauma to surrounding nerves and tissue.

For use in surgery, the blade can be provided in a sterile packaging. The packaging integrity should be maintained to ensure sterility throughout shelf life. The packaging must provide physical protection during storage and transport. The cannulas, obturators, obturator handle, and spatulas can be provided in a tray that can be sterilized.

Referring to FIGS. 16-20, 21A and 21B, about a 2 cm incision I can be made such as by a knife K over the cubital tunnel, posterior to the medial epicondyle in an elbow E. The surgeon can dissect down to the deep fascia. The tissue can be elevated to create space between the deep fascia and the subcutaneous tissue proximally and distally. The medial epicondyle can be palpated and the cubital tunnel opened to locate the ulnar nerve. Obturator 40 can be connected to obturator handle 50 with grip 52 by inserting the handle insert of obturator 40 into locking chamber 54 and insert support body 42 of obturator 40 into slotted cannula 30 through base aperture 34A of base 34 of obturator 40. The skin can be lifted, and obturator 40 and cannula 30 can be inserted into the incision I and into or around the cubital tunnel.

Retractor 70 attached to cannula 30 using retractor arm 76 can be used to lift the skin and subcutaneous tissue and nerves. Trigger 74 can be used to move retractor arm 76 between different positions to lift the skin and subcutaneous tissue and nerves. The length of release of the cubital tunnel that is needed can be determined. Obturator 40 can be removed with handle 50. An endoscope 80 can be inserted in access opening AO between base 34 of cannula 30 and support arms 78 and retractor arm 76 of retractor 70 to confirm that no superficial nerves are in danger of being damaged. Endoscope 80 can be inserted into aperture 34A of cannula 30 having slots 38 (See FIG. 2) within the insertion body 32 to confirm that the ulnar nerve is located beneath cannula 30.

Figure 21A:
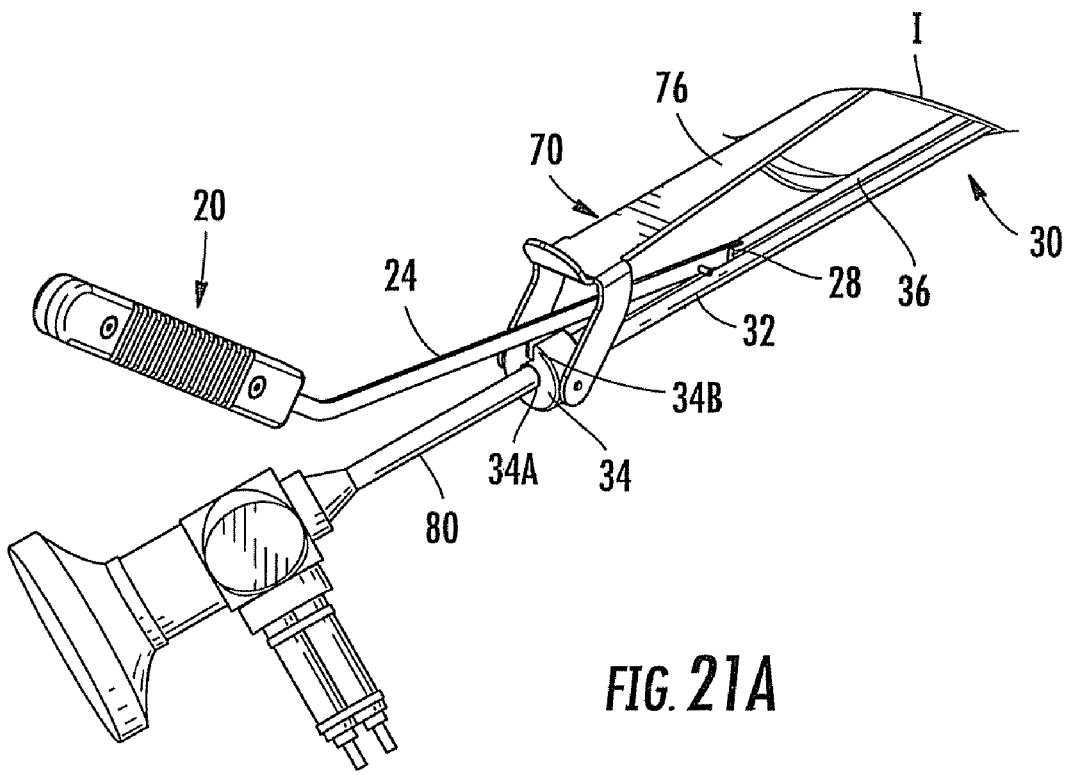
Figure 21B:
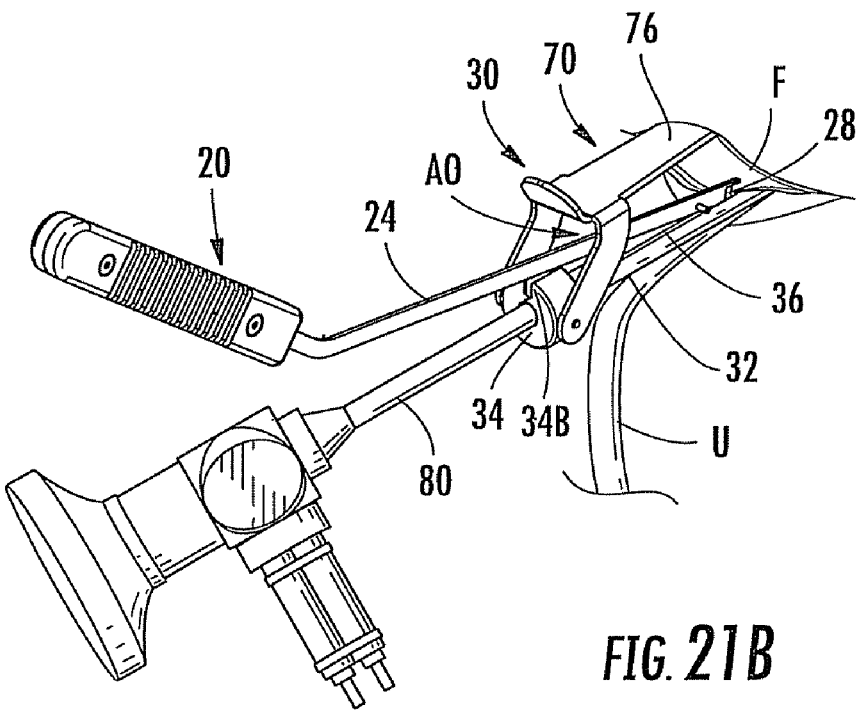

FIG. 21A shows blade 20 engaging cannula 30 without showing the ulnar nerve and the fascia surrounding it. FIG. 21B shows blade 20 engaging cannula 30, while cannula 30 is placed between fascia F and ulnar nerve U. Body 24 of blade 20 can be inserted into slot 34B on base 34 of cannula 30 and the cutting edge can reside in continuous slot 36 in insertion body 32. Endoscope 80 can be used to visualize fascia F and blade 20 by having endoscope 80 inserted through aperture 34A and into chamber 35 (see FIG. 3) of the cannula 30. It can be determined through the use of endoscope 80 whether cannula 30 is in proper alignment with insertion body 32 disposed between fascia F and ulnar nerve U. Fascia F can then be incised such as by blade 20. As described above, the bottom surface of cannula 30 can be substantially flat, concave, or of any other suitable shape. After cutting, blade 20 can be removed and endoscope 80 can be used to confirm that fascia F is incised along the tunnel and that ulnar nerve U is sufficiently released. At this point, endoscope 80 and cannula 30 can be removed using retractor 70. The distal portion of the cubital tunnel release can then be performed as described above.

Referring to FIGS. 22, 23, 24A, 24B, 24C, 24D, 25A, 25B and 25C, another embodiment of an obturator 100 will be described in more detail. The obturator 100 includes an indexing rod 102 and an indexing washer 104. The indexing rod 102 and indexing washer 104 can be separable from one another. Alternatively, the indexing rod 102 and indexing washer 104 can be attached to each other so that they are inseparable or can be integral to one another.

The indexing rod 102 can include a support body 106 and a handle inert 108. Support body 106 can be separated from the handle insert 108 by a stopper 110. Handle insert 108 can be thicker in diameter than support body 106. Stopper 110 can be used to hold the indexing washer 104 in place and at least a portion of the stopper 110 can extend farther outward than the outer diameter of the handle insert 108. For example, the stopper 110 can have a larger diameter than handle insert 108. Further, a stopper 110 that has a circular cross-section can include a locking mechanism that engages the indexing washer 104 to prevent the indexing washer 104 from rotating around the stopper 110 and the handle insert 108.

Support body 106 of indexing rod 102 can have a head end 106A. Head end 106A of obturator 100 can have angled surfaces that end in a relatively blunt lead point 106B to serve as a lead in for the device. For example, head end 106A can have four angled surfaces to help lead in the device. These angled surfaces preferably do not have sharp edges. The angled surfaces can vary in the angle of the surfaces as will be explained further below.

Each obturator 100 can be provided with handle insert 108 which can have a coupling configuration 118. The coupling configuration 118 can be accepted by a standard A/O couple within an obturator handle, such as an obturator 50 described above. For example, coupling configuration 118 can include a keyway 118A. Keyway 118A can extend over the entire width of handle insert 108. A groove 118B can extend around the remaining circumference of handle insert 108. The distal end of handle insert 108 can have tapered sides 118C. Keyway 118A, groove 118B and/or the tapered sides 118C of the coupling configuration 118 can all help to secure obturator 100 to an obturator handle through the couple therein.

The indexing washer 104 can include a washer body 120 and a locking protrusion 122. The indexing washer 104 can be used to lock the obturator 100 in place in a cannula, such as cannula 30 described above. For example, the locking protrusion 122 can fit into the guide slot 34B of the cannula 30 shown in FIG. 4. The locking protrusion 122 can facilitate the obturator 100 being secure in the cannula 30 during insertion into a patient. In one embodiment, the locking protrusion 122 can hold the obturator 100 in a fixed position relative to the cannula 30 in which it is inserted to provide a desired alignment of the lead point 106B of the support body 106 with the cannula 30. In another embodiment, the indexing washer 104 can be removed from the indexing rod 102 and the indexing rod 102 can be used alone as the obturator to permit rotation of the obturator in the cannula. In another embodiment, the indexing rod 102 is free to rotate in the indexing washer 104.

The locking protrusion 122 can be on any shape or size that facilitates the securing of the obturator in the cannula.

Washer 104 can have at least one bore therein that permits sliding engagement with the handle insert 108 of the obturator 100. The bore can abut the stopper 110 to prevent the indexing washer 104 from also sliding over the support body 106.

For example, indexing washer body 120 can have concentric bores 124 and 126 therein. The first bore 124 can be smaller than the second bore 126 and can extend through a first end 120A of the washer body 120. The second bore 126 can extend through a second end 120B and can be larger in diameter than the first bore 124. The two bores 124, 126 can create an abutment shelf 128. The indexing washer 104 can be slid over the handle insert 108 with the larger second bore 126 leading. The smaller first bore 124 can be of a diameter that permits washer body 120 to snugly fit over the handle insert 108 in the bore 124. The larger second bore 126 can be of a diameter that permits the washer body 120 to snugly fit over the stopper 110 at the second bore 126. In this manner, the abutment shelf 128 abuts against the stopper 110. The bores 124, 126 in the embodiment shown have a circular cross-section. It is understood that the bores may have other cross-sectional shapes, such as a square or rectangular cross-section, that permits the handle insert and the stopper to be secured in the respective bores. In such embodiments, the handle insert and stopper can have matching cross-sectional shapes.

Figure 22:
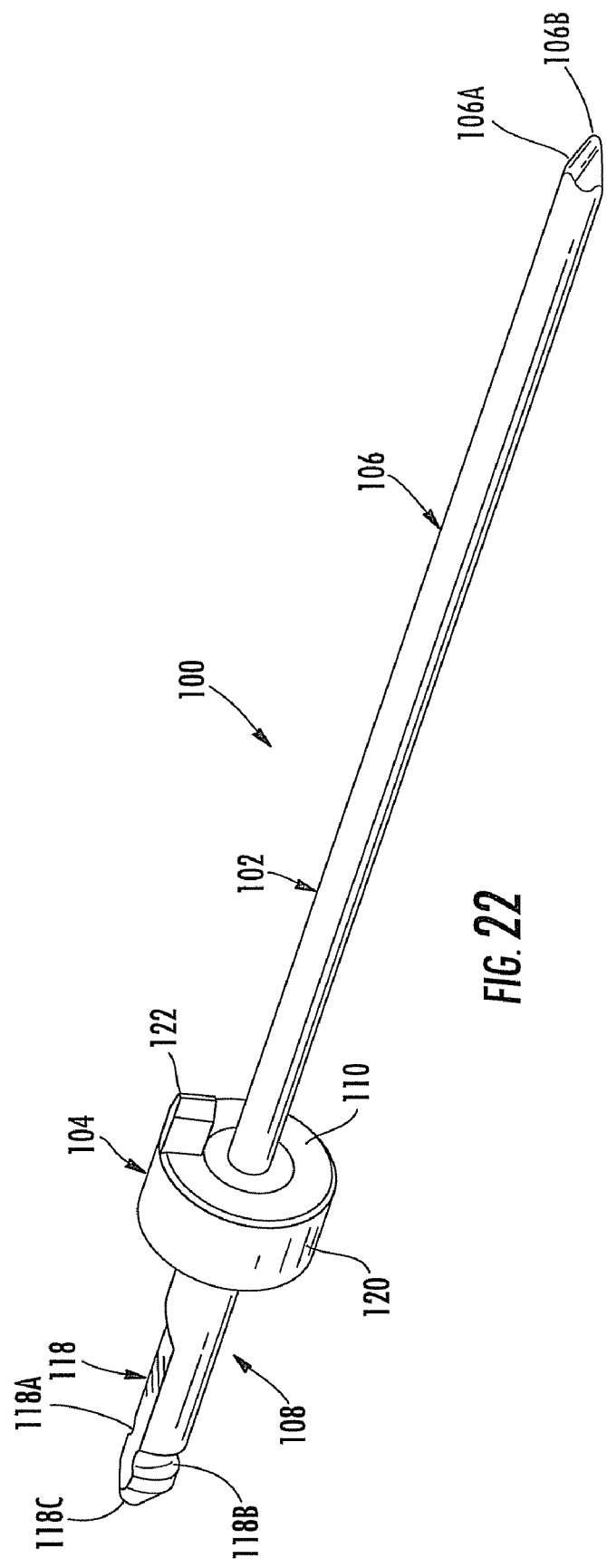
FIG. 22 illustrates a perspective view of an embodiment of an obturator that can be included in accordance with the subject matter herein.
Figure 24A:
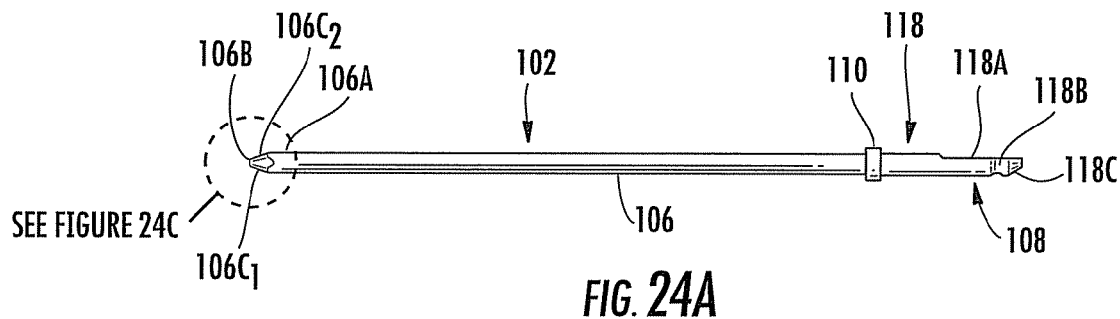
FIGS. 24A and 24B illustrate side views of an embodiment of an indexing rod for the obturator according to FIG. 22.
Figure 24B:
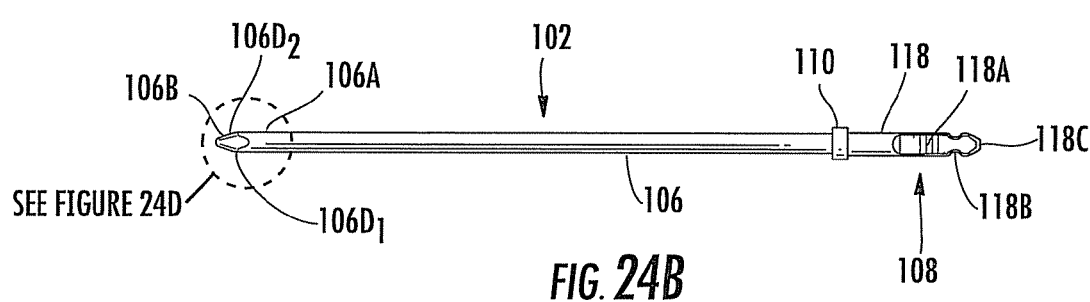
Figure 24C:
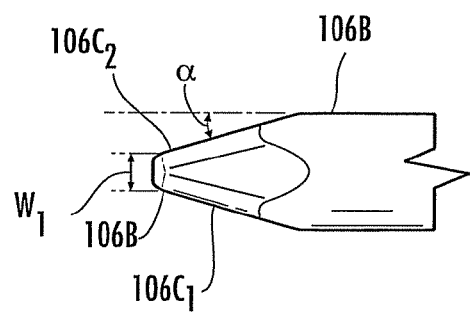
FIGS. 24C and 24D illustrate side views of the head end of the indexing rod according to FIGS. 24A and 24B.
Figure 24D:
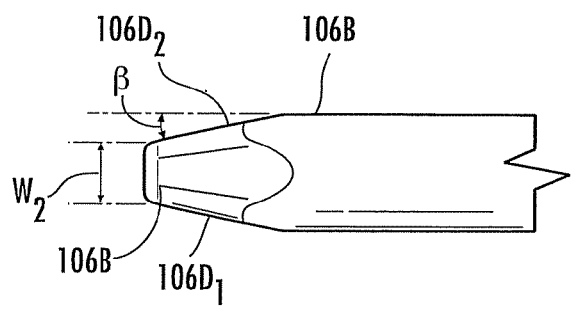
Figure 25A:
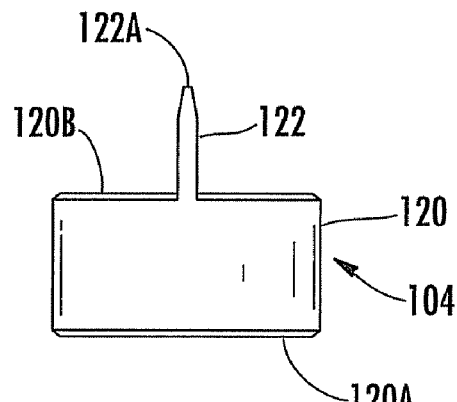
FIG. 25A illustrates a top view of an embodiment of an indexing washer for the obturator according to FIG. 22.
Figure 25B:
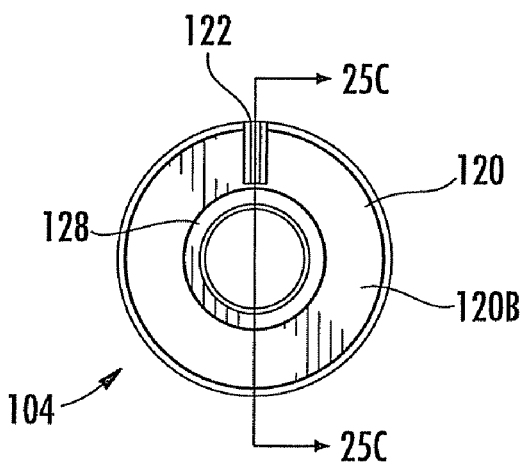
FIG. 25B illustrates a front view of the embodiment of the indexing washer according to FIG. 25A.
Figure 25C:
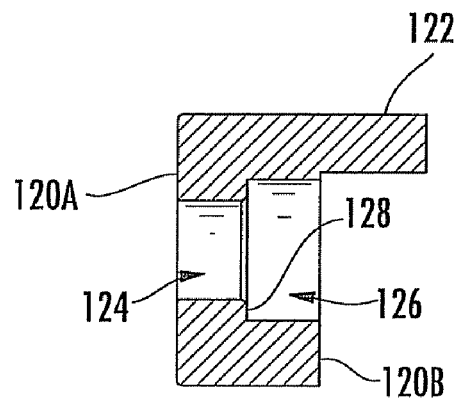
FIG. 25C illustrates a cross-sectional view of the embodiment of the indexing washer taken along the line AA of FIG. 25B.

Receiving end 56 of the locking chamber portion 54 of the obturator handle 50 has the aperture 56A and chamber 57 (see FIGS. 6-8) therein to receive the coupling configuration 118 of handle insert 108 of obturator 100 (see FIGS. 22 and 23). After the indexing washer 104 is placed on the indexing rod 102, the obturator handle 50 can engage the handle insert 108 for the obturator 100. The key 56B of receiving end 56 can mate with keyway 118A of handle insert 108. If keyway 118A aligns with key 56B, then tapered sides 118C can pass into aperture 56A without obstruction. As stated above, receiving end 56 can also include at least one spring-loaded locking ball 56C that can be depressible into the wall of chamber 57, but is biased out into chamber 57. As tapered sides 118C of handle insert 108 pass locking ball 56C, tapered sides 118C can depress locking ball 56C at such positions along tapered sides 118C of sufficient width to allow tapered sides 118 to pass locking ball 56C. After tapered sides 118C pass locking ball 56C, locking ball 56C can spring into groove 118B to effectively lock obturator 100 into obturator handle 50. To release obturator 100 from obturator handle 50, slide barrel 55 can be configured to engage locking ball 56C so that when slide barrel 55 is pushed forward in direction G (see FIG. 8), locking ball 56C is withdrawal into chamber 57. In this manner, handle insert 108 and obturator 100 can be released from obturator handle 50.

Support body 106 of obturator 100 (see FIGS. 22 and 23) can be inserted through the aperture in base 34 and chamber 35 of cannula 30 (see FIGS. 2-4) such that head end 106A extends out through the aperture in lead end 37 of cannula 30 in a similar manner as shown in FIG. 10. Head end 106A with its angled surfaces and lead point 106B facilitates guiding cannula 30 to the proper location within the elbow between the ulnar nerve and the fascia surrounding it. Further, the rest of support body 106 of obturator 100 buttresses insertion body 32 of cannula 30 during insertion into the elbow of the patient.

The diameter of each obturator 100 can be configured to fit snugly inside the inner diameter of the respective corresponding cannula 30. The effective length of each obturator 100 can be such that it extends past lead end 37 of the respective corresponding cannula 30 in a similar manner to the obturator 40 shown in FIG. 10 to provide an unobstructed head end 106A and lead point 106B obturator 100 for guiding the insertion. For example, as described above in relation to FIG. 10, the effective length of a large obturator can be such that the distance from lead point 106B of head end 106A to lead end 37 of the large cannula can be greater than for a smaller obturator.

As shown in FIGS. 24A-24D, head end 106A may have different angled sides toward lead point 106B such that the lead point 106B is wider on one side and more pointed on another side. For example, head end 106A can have sides $106C_1$ and $106C_2$ that are angled at an angle α, while head end 106A can have sides $106D_1$ and $106D_2$ that are angled at an angle β. Angle α can be greater than angle β, such that a width $w_1$ of the lead point 106B on the sides that are created by the angled sides $106C_1$ and $106C_2$ is smaller than a width $w_2$ of the lead point 106B on the sides that are created by the angled sides $106D_1$ and $106D_2$. The sides of different widths $w_1$, $w_2$ of the lead point 106B can be properly aligned with the coupling configuration 118 to obtain a desired alignment of the sides of different width $w_1$, $w_2$ of the lead point 106B with a cannula 30. For example, one of the sides of lead point 106B with width $w_2$ can be aligned with the keyway 118A to align that side of lead point 106B with width $w_2$ with the guide slot 34B in cannula 30. Other alignment configurations of the lead point 106B and the coupling configuration 118 and the position of the cannula 30 are possible.

As with cannulas 30, obturators 40, 100 can be made from surgical grade stainless steel. Surgical grade stainless steel has been shown to have a proven clinical history and is traceable to accepted material standards for bio-compatibility, strength, etc. Further, surgical grade stainless steel can be sterilized in a surgical setting.

As described above, cannula 30, obturator 40, 100, obturator handle 50, and spatula 60 can be reusable. After each use, these apparatuses can be reprocessed. Cannula 30, obturator 40, 100, obturator handle 50, and spatula 60 can be provided non-sterile and sterilized prior to surgery. All products should be cleaned, decontaminated and sterilized before use.

The above description with reference to ulnar nerve release by the surgical release apparatuses, systems and methods disclosed herein is provided as one example of applicability of the present disclosure. As noted previously, the surgical release apparatuses, systems and methods disclosed herein can be used in any suitable application, such as for example, endoscopic release of other nerves or cutting of other tissue using the instrumentation as described.

Embodiments of the present disclosure shown in the drawings and described above are exemplary of numerous embodiments that can be made within the scope of the appending claims. It is contemplated that the apparatuses, systems and related methods can comprise numerous configurations other than those specifically disclosed. The scope of a patent issuing from this disclosure will be defined by these appending claims.

What is claimed is:

1. A surgical release system comprising:
    a cannula having a base and an insertion body, the insertion body extending from the base and terminating at a lead end, the cannula having a chamber disposed through the base and the insertion body, and the cannula having a movable retractor attached to the base and configured to facilitate creation of space between the insertion body of the cannula and the retractor, wherein the retractor comprises a retractor arm extending from the base towards the lead end of the insertion body, the retractor arm being movable toward and away from the insertion body such that a lead end of the retractor arm is engageable with the lead end of the insertion body;
    an obturator having a support body configured for insertion into the chamber of the cannula to facilitate the guidance of the insertion body of the cannula; and
    a blade having a handle, a blade body, and a cutting edge, the blade configured for engaging and being guided by the cannula for the cutting edge to make an incision.

2. The surgical release system according to claim 1, wherein the cannula includes a continuous slot extending along a side of the insertion body to guide the cutting edge of the blade during incision.

3. The surgical release system according to claim 2, wherein the cannula includes a series of slots extending along a side of the insertion body opposite a side in which the continuous slot resides, the series of slots configured to provide a visualization through the cannula.

4. The surgical release system according to claim 1, wherein the cannula includes a guide slot in the base configured for receiving the body of the blade during the incision.

5. The surgical release system according to claim 1, wherein the retractor arm is narrow at the lead end and wider at a base end.

6. The surgical release system according to claim 5, wherein the retractor arm includes support arms that connect to pivotal points on the base of the cannula, the pivotal points permitting the retractor arm to rotate about the pivotal points.

7. The surgical release system according to claim 6, wherein the retractor arm, support arms and the base of the cannula define an access opening.

8. The surgical release system according to claim 7, wherein the retractor arm includes a trigger that can be manually manipulated to rotate the retractor arm in a first direction and a second direction.

9. The surgical release system according to claim 1, wherein the support body of the obturator is extendable through the chamber of the cannula and past the lead end of the insertion body of the cannula.

10. The surgical release system according to claim 1, further comprising an obturator handle into which the obturator can be inserted and removed.

11. The surgical release system according to claim 10, wherein the obturator includes a handle insert that is distal from a head end of the support body, the handle insert configured to engage and disengage the obturator handle.

12. The surgical release system according to claim 1, wherein the blade includes safety prongs disposed on either side of the cutting edge and extending outward therefrom.

13. The surgical release system according to claim 1, further comprising one or more spatulas configured to provide guidance to the blade.

14. The surgical release system according to claim 1, wherein a bottom surface of the cannula is at least one of a concave or substantially flat shape.

15. The surgical release system according to claim 1, wherein the obturator further comprises a locking protrusion that is configured to engage a guide slot in the base of the cannula.

16. The surgical release system according to claim 1, wherein the obturator further comprises an indexing washer and an indexing rod that includes the support body and a stopper, the indexing washer configured to engage the indexing rod such that the indexing washer abuts the stopper and the indexing washer including a locking protrusion that is configured to engage a guide slot in the base of the cannula.

17. The surgical release system of claim 1, wherein the retractor arm terminates at least proximate the lead end of the insertion body.

18. A surgical release system comprising:
a small cannula and a large cannula, each cannula having a base and an insertion body, the insertion body extending from the base and terminating at a lead end, each cannula having a chamber disposed through the base and the insertion body, and each cannula having a movable retractor attached to the base and configured to facilitate creation of space between the insertion body of the cannula and the retractor, wherein each movable retractor comprises a retractor arm extending from the base towards the lead end of the insertion body, wherein the retractor arm is movable toward and away from each respective insertion body such that a lead end of the retractor arm is engageable with the lead end of the insertion body;
a small obturator and a large obturator, each obturator having a support body configured for insertion into the chamber of the corresponding sized cannula to facilitate guiding the respective cannula;
a blade having a handle, a blade body, and a cutting edge, the blade configured for engaging and being guided by the respective cannula for the cutting edge to make an incision; and
a small spatula and a large spatula, each spatula configured to provide guidance to the blade.

19. The surgical release system according to claim 18, wherein each cannula includes a continuous slot extending along a side of the insertion body to guide the cutting edge of the blade during incision.

20. The surgical release system according to claim 19, wherein each cannula includes a series of slots extending along a side of the insertion body opposite the side in which the continuous slot resides, the series of slots configured to provide a visualization through the cannula.

21. The surgical release system according to claim 18, wherein each cannula includes a guide slot in the base configured for receiving the body of the blade during the incision.

22. The surgical release system according to claim 18, wherein each retractor arm is narrow at the lead end and wider at a base end.

23. The surgical release system according to claim 22, wherein each retractor arm includes support arms that connects to pivot points on the base of the cannula, the pivot points permitting the retractor arm to rotate about the pivot points.

24. The surgical release system according to claim 23, wherein each retractor arm, its associated support arms and the base of the respective cannula define an access opening.

25. The surgical release system according to claim 24, wherein each retractor arm includes a trigger that can be manually manipulated to rotate the respective retractor arm in a first direction and a second direction.

26. The surgical release system according to claim 18, wherein the support body of each obturator is extendable through the chamber and past the lead end of the insertion body of the respective cannula.

27. The surgical release system according to claim 18, further comprises a removable obturator handle into which the obturators can be inserted.

28. The surgical release system according to claim 27, wherein each obturator includes a handle insert that is distal from a head end of the support body, each handle insert configured to engage and disengage the obturator handle.

29. The surgical release system according to claim 18, wherein the blade includes safety prongs disposed on either side of the cutting edge and extending outward therefrom.

30. The surgical release system according to claim 18, wherein a bottom surface of the cannula is at least one of a concave or substantially flat shape.

31. The surgical release system according to claim 18, wherein each obturator further comprises a locking protrusion that is configured to engage a guide slot in the base of the cannula.

32. The surgical release system according to claim 18, wherein each obturator further comprises an indexing washer and an indexing rod that includes the support body and a stopper, the indexing washer configured to engage the indexing rod such that the indexing washer abuts the stopper and the indexing washer including a locking protrusion that is configured to engage a guide slot in the base of the cannula.

33. A cannula comprising:
a base;
an insertion body extending from the base and terminating at a lead end, where a chamber is at least partially disposed through the base and the insertion body; and
a movable retractor attached to the base, the retractor configured to facilitate creation of space between the insertion body of the cannula and the retractor, wherein the retractor comprises a retractor arm extending from the base towards the lead end of the insertion body, and wherein the retractor arm is movable toward and away from the insertion body such that a lead end of the retractor arm is engageable with the lead end of the insertion body.

34. The cannula according to claim 33, wherein the cannula includes a continuous slot extending along a side of the insertion body to guide a cutting edge of a blade during incision.

35. The cannula according to claim 34, wherein the cannula includes a series of slots extending along a side of the insertion body opposite the side in which the continuous slot resides, the series of slots configured to provide a visualization through the cannula.

36. The cannula according to claim 33, wherein the cannula includes a guide slot in the base configured for receiving a body of a blade during the incision.

37. The cannula according to claim 33, wherein the retractor arm is narrow at the lead end and wider at a base end.

38. The cannula according to claim 37, wherein the retractor arm includes support arms that connects to pivotal points on the base of the cannula, the pivotal points permitting the retractor arm to rotate about the pivotal points.

39. The cannula according to claim 38, wherein the retractor arm, support arms and the base of the cannula define an access opening.

40. The cannula according to claim 39, wherein the retractor arm includes a trigger that can be manually manipulated to rotate the retractor arm in a first direction and a second direction.

41. The cannula according to claim 33, wherein a bottom surface of the cannula is at least one of a concave or substantially flat shape.

42. A surgical release system comprising:
a cannula having a base and an insertion body, the insertion body extending from the base and terminating at a lead end, the cannula having a chamber disposed through the base and the insertion body, and the cannula having a movable retractor attached to the base and configured to facilitate creation of space between the insertion body of the cannula and the retractor, wherein the retractor comprises a retractor arm extending from the base towards the lead end of the insertion body such that a lead end of the retractor arm and the lead end of the insertion body have a similar width configured for at least partial insertion into a surgical incision;

an obturator having a support body configured for insertion into the chamber of the cannula to facilitate the guidance of the insertion body of the cannula; and a blade having a handle, a blade body, and a cutting edge, the blade configured for engaging and being guided by the cannula for the cutting edge to make an incision.

* * * * *